US006080750A

United States Patent [19]

Hisaki et al.

[11] Patent Number: 6,080,750

[45] Date of Patent: Jun. 27, 2000

[54] PYRIMIDINE COMPOUND AND ANTI-ROTAVIRUS COMPOSITION

[75] Inventors: Masakatsu Hisaki, Hikone; Yoichiro Ohta, Takatsuki; Kenji Kawanishi, Osaka; Yasuko Ichigobara, Ibaraki; Fuzuki Iwakura, Osaka; Masanobu Azuma; Tatsuo Suzutani, both of Asahikawa; Manabu Node, Hirakata; Kiyoharu Nishide, Kouka-gun, all of Japan

[73] Assignee: Nippon Shoji Kaisha Ltd., Osaka, Japan

[21] Appl. No.: 08/852,118

[22] Filed: May 6, 1997

[30] Foreign Application Priority Data

May 9, 1996 [JP] Japan .................................... 8-115147

[51] Int. Cl.[7] ...................... C07D 239/48; C07D 239/47; A61K 31/505

[52] U.S. Cl. .......................... 514/275; 544/319; 544/323; 544/320; 544/322; 544/326; 544/329; 544/332; 514/272; 514/269; 514/256

[58] Field of Search .................................... 544/319, 320, 544/322, 323, 326, 330; 514/256, 269, 272, 275

[56] References Cited

U.S. PATENT DOCUMENTS

| | | | |
|---|---|---|---|
| 3,034,954 | 5/1962 | Darlington | 167/33 |
| 4,523,945 | 6/1985 | Mengel et al. | 71/92 |
| 4,939,252 | 7/1990 | Schwartz | 544/321 |

FOREIGN PATENT DOCUMENTS

| | | |
|---|---|---|
| 0 116 961 | 8/1984 | European Pat. Off. . |
| 0 366 059 | 5/1990 | European Pat. Off. . |
| 1143167 | 2/1969 | United Kingdom . |

OTHER PUBLICATIONS

Parkanyi et al., "Synthesis of Acyclic Nucleoside Analogs of 6–Substituted 2–Aminopurines and 2–Amino–8–azapurines", *J. Heterocylic Chem.,* 27, 1409–1413 (1990).

Eger et al., "Sythesis of New Acyclic Pyrimidine Nucleoside Analogs as Potential Antiviral Drugs", *J. Med. Chem.,* 37, 3057–3061 (1994).

Oonishi et al., "Preparation of 6–(((1', 2'–bis(hydroxymethyl)propan–1'–yl)methyl)pyrimidine derivatives as intermediates for antiviral purine nucleoside analogs", *Chemical Abstracts,* 124, No. 25, 1405 (1996).

Botta et al, Chemical Abstracts, vol. 122, entry 81278 (1995).

*Primary Examiner*—John M. Ford
*Attorney, Agent, or Firm*—Leydig, Voit & Mayer, Ltd.

[57] ABSTRACT

A pyrimidine compound of the formula [I]

[I]

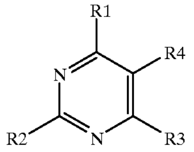

wherein R1 is H, $C_1$–$C_4$ lower alkyl, halogen atom, —OH, $C_1$–$C_4$ lower alkoxy, $C_1$–$C_6$ hydroxy(lower)alkoxy or —$NH_2$; R2 is H, —$NH_2$ or —$NHCOCH_3$; R3 is —NR5 $(CH_2)$i—$CH_2OH$; R4 is H, halogen atom, —$NH_2$, —CN, —CHO, —$CH_2OH$, —COOH, —$CH_2NH_2$, —$CONH_2$ or —CH=N—A wherein A is —OH, $C_1$–$C_4$ lower alkyl or $C_1$–$C_4$ lower alkoxy; R5 is H or $C_1$–$C_4$ lower alkyl; and i is an integer of 1 to 4, and an anti-rotavirus agent comprising, as an active ingredient, a compound of the formula [I] wherein R3 is a group selected from the following:

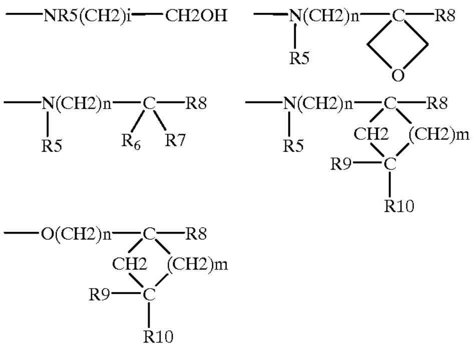

The novel pyrimidine compound of the present invention and related derivatives thereof have superior anti-rotavirus action and are useful for the prophylaxis and treatment of rotaviral diseases.

6 Claims, No Drawings

PYRIMIDINE COMPOUND AND ANTI-ROTAVIRUS COMPOSITION

TECHNICAL FIELD OF THE INVENTION

The present invention relates to a novel pyrimidine compound and an anti-rotavirus agent. More particularly, the present invention relates to a novel pyrimidine compound having an anti-rotaviral action and useful as an agent for the prophylaxis and treatment of rotaviral diseases, a pharmacologically acceptable salt thereof and an anti-rotavirus agent containing a novel pyrimidine compound or a related derivative as an active ingredient. The present invention also relates to a method for the prophylaxis and treatment of rotaviral diseases, which comprises administering said novel pyrimidine compound or a related derivative.

BACKGROUND OF THE INVENTION

There are numerous viral diseases for which no satisfactory pharmaceutical agent is available in terms of efficacy and safety, and the development of superior antiviral agents has been desired.

Conventionally known pyrimidine related derivatives having a cycloalkyl ring include the following. U.S. Pat. No. 4,939,252 discloses a cyclopentenecarbinol compound substituted by a pyrimidinylamino group, as an intermediate for producing an antiviral agent known as carbovir.

U.S. Pat. Nos. 5,153,352 and 5,246,931 disclose a pyrimidine derivative having a cyclobutylamino group, as an intermediate for synthesizing carbocyclic nucleoside analog.

U.S. Pat. No. 4,523,945 discloses a pyrimidine derivative having a cyclopropylmethylamino group, which is useful as herbicide or microbicidal agent.

Yet, a compound having a structure of the pyrimidine compound of the present invention and having an anti-rotaviral action has not been reported.

A rotavirus is an RNA virus belonging to the reovirus family and known to be the pathogenic virus of infant diarrhea (white diarrhea). The virus can be found in human in the flux of infants with acute gastroenteritis.

There is currently available no satisfactory medicament for the treatment of rotaviral diseases, and the development of a new anti-rotavirus agent is desired, motivated by which various studies have been undertaken.

SUMMARY OF THE INVENTION

It is therefore an object of the present invention to provide a novel compound useful as an anti-rotavirus agent.

Another object of the present invention is to provide an anti-rotavirus agent containing said novel compound or a related derivative.

A still another object of the present invention is to provide a method for the prophylaxis and treatment of rotaviral diseases.

As a result of the study and investigation in view of the above-mentioned situation, it has been found according to the present invention that the novel pyrimidine compound and related derivatives of the present invention have superior anti-rotaviral action.

Accordingly, the present invention provides the following.

(1) A pyrimidine compound of the formula [I]

[I]

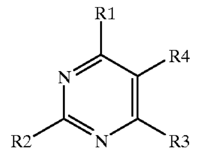

wherein

R1 is H, $C_1$–$C_4$ lower alkyl, halogen atom, —OH, $C_1$–$C_4$ lower alkoxy, $C_1$–$C_6$ hydroxy(lower)alkoxy or —$NH_2$;

R2 is H, —$NH_2$ or —$NHCOCH_3$;

R3 is —$NR5(CH_2)i$—$CH_2OH$;

R4 is H, halogen atom, —$NH_2$, —CN, —CHO, —$CH_2OH$, —COOH, —$CH_2NH_2$, —$CONH_2$ or —CH═N—A wherein A is —OH, $C_1$–$C_4$ lower alkyl or $C_1$–$C_4$ lower alkoxy;

R5 is H or $C_1$–$C_4$ lower alkyl; and i is an integer of 1 to 4, and pharmacologically acceptable salts thereof.

(2) A pharmaceutical composition comprising the pyrimidine compound of (1) above or a pharmacologically acceptable salt thereof, and a pharmacologically acceptable carrier.

(3) An anti-rotavirus agent comprising the pyrimidine compound of (1) above or a pharmacologically acceptable salt thereof as an active ingredient.

(4) An agent for the prophylaxis and treatment of rotaviral diseases, comprising the pyrimidine compound of (1) above or a pharmacologically acceptable salt thereof as an active ingredient.

(5) An anti-rotavirus agent comprising a pyrimidine compound of the formula [I']

[I']

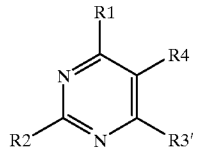

wherein

R1 is H, $C_1$–$C_4$ lower alkyl, halogen atom, —OH, $C_1$–$C_4$ lower alkoxy, $C_1$–$C_6$ hydroxy(lower)alkoxy or —$NH_2$;

R2 is H, —$NH_2$ or —$NHCOCH_3$;

R3' is a group selected from the following (a) to (e):

(a)

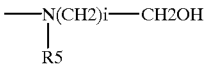

(b)

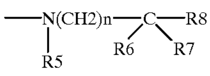

(c)

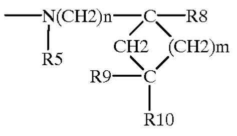

-continued (d)

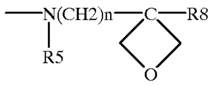

(e)

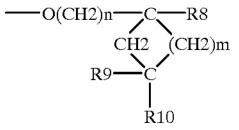

wherein

R5 is H or $C_1$–$C_4$ lower alkyl,

R6 and R7 are the same or different and each is $C_1$–$C_4$ lower alkyl,

R8 is H, —OH, $C_1$–$C_4$ hydroxy(lower)alkyl or —$CH_2OC(O)CH_3$,

R9 is H, —OH, $C_1$–$C_4$ lower alkyl, $C_1$–$C_4$ hydroxy(lower)alkyl, $C_1$–$C_4$ lower alkoxy, vinyl, —$O(CH_2)$k-R where R is aromatic ring optionally having, on its ring, a substituent selected from $C_1$–$C_4$ lower alkyl, halogen atom and $C_1$–$C_4$ lower alkoxy, and k is an integer of 0 to 4, or —$(CH_2)$j-R' where R' is benzoyloxy or aromatic ring optionally having, on its ring, a substituent selected from $C_1$–$C_4$ lower alkyl, halogen atom and $C_1$–$C_4$ lower alkoxy, and j is an integer of 0 to 6, R10 is H, —OH or $C_1$–$C_4$ lower alkoxy, R9 and R10 may form a methylene group (=$CH_2$) or a carbonyl (C=O) together with the carbon atom to which they are bonded, in the formulas (c) and (e), cycloalkyl ring may have a double bond at an optional position in the ring, i is an integer of 1 to 4, n is an integer of 0 to 4, and m is an integer of 0 to 4; and R4 is H, halogen atom, —$NH_2$, —CN, —CHO, —$CH_2OH$, —COOH, —$CH_2NH_2$, —$CONH_2$ or —CH=N—A where A is —OH, $C_1$–$C_4$ lower alkyl or $C_1$–$C_4$ lower alkoxy, exclusive of when n is 0 and R8 is H;

or a pharmacologically acceptable salt thereof as an active ingredient.

(6) The anti-rotavirus agent of the above (5), wherein j is an integer of 0 to 4.

(7) An agent for the prophylaxis and treatment of rotaviral diseases, comprising the pyrimidine compound of the formula [I'] of the above (5) or a pharmacologically acceptable salt thereof as an active ingredient.

(8) A method for the prophylaxis and treatment of rotaviral diseases, which comprises administering an effective amount of the pyrimidine compound of the formula [I'] of the above (5) or a pharmacologically acceptable salt thereof.

(9) Use of the pyrimidine compound of the formula [I'] of the above (5) or a pharmacologically acceptable salt thereof in the production of an anti-rotavirus medicament.

(10) Use of the pyrimidine compound of the formula [I'] of the above (5) or a pharmacologically acceptable salt thereof in the production of a medicament for the prophylaxis and treatment of rotaviral diseases.

DETAILED DESCRIPTION OF THE INVENTION

In the above-mentioned formula [I] of the present invention, $C_1$–$C_4$ lower alkyl represented by R1 may be linear or branched, and is exemplified by methyl, ethyl, n-propyl, isopropyl, n-butyl and isobutyl, with preference given to methyl and ethyl, and more preference given to methyl. The halogen atom is exemplified by chlorine, bromine, fluorine and iodine atoms, with preference given to chlorine and fluorine atoms. The $C_1$–$C_4$ lower alkoxy may be linear or branched, and is exemplified by methoxy, ethoxy, n-propoxy, isopropoxy and n-butoxy, with preference given to methoxy and ethoxy, and more preference given to methoxy. The $C_1$–$C_6$ hydroxy(lower)alkoxy may have a linear or branched alkoxy moiety, or may have a cycloalkyl ring. Examples thereof include 2-hydroxyethoxy, 3-hydroxypropoxy, 4-hydroxybutoxy and 1-hydroxymethyl-cyclobutyl-1-methoxy.

The halogen atom at R4 is exemplified by chlorine, bromine, fluorine and iodine atoms.

A in —CH=N—A at R4 is hydroxy, $C_1$–$C_4$ lower alkyl or $C_1$–$C_4$ lower alkoxy. The $C_1$–$C_4$ lower alkyl represented by A may be linear or branched, and is exemplified by methyl, ethyl, n-propyl, isopropyl, n-butyl and isobutyl. The $C_1$–$C_4$ lower alkoxy represented by A may be linear or branched, and is exemplified by methoxy, ethoxy, n-propoxy, isopropoxy, n-butoxy and isobutoxy. A is preferably hydroxy.

The $C_1$–$C_4$ lower alkyl at R5 may be linear or branched, and is exemplified by methyl, ethyl, n-propyl, isopropyl, n-butyl and isobutyl.

In the aforementioned formula [I'] of the present invention, the groups represented by R1, R4 and R5 are exemplified by those shown with regard to formula [I].

The $C_1$–$C_4$ lower alkyl at R6 or R7 may be linear or branched, and is exemplified by methyl, ethyl, n-propyl, isopropyl, n-butyl and isobutyl, with preference given to methyl, ethyl and propyl, and more preference given to methyl and ethyl.

The $C_1$–$C_4$ hydroxy(lower)alkyl at R8 may have a linear or branched alkyl moiety. Examples thereof include hydroxymethyl, 1-hydroxyethyl, 1-methyl-2-hydroxyethyl, 1-hydroxypropyl, 2-hydroxyethyl, 3-hydroxypropyl and 4-hydroxybutyl, with preference given to hydroxymethyl, 1-hydroxyethyl, 1-methyl-2-hydroxyethyl and 2-hydroxyethyl, and more preference given to hydroxymethyl, 1-hydroxyethyl and 2-hydroxyethyl.

The $C_1$–$C_4$ lower alkyl at R9 may be linear or branched, and is exemplified by methyl, ethyl, n-propyl, isopropyl, n-butyl and isobutyl, with preference given to methyl, ethyl, n-propyl and isopropyl, and more preference given to n-propyl and isopropyl: the $C_1$–$C_4$ hydroxy(lower)alkyl may have a linear or branched alkyl moiety. Examples thereof include hydroxymethyl, 1-hydroxyethyl, 2-hydroxyethyl, 3-hydroxypropyl and 4-hydroxybutyl, with preference given to hydroxymethyl, 1-hydroxyethyl, 2-hydroxyethyl and 3-hydroxypropyl, and more preference given to hydroxymethyl: the $C_1$–$C_4$ lower alkoxy may be linear or branched, and is exemplified by methoxy, ethoxy, n-propoxy, isopropoxy and n-butoxy, with preference given to methoxy and ethoxy, and more preference given to methoxy.

The R in —$O(CH_2)$k-R which is represented by R9 is an aromatic group optionally having a substituent on the ring. The $C_1$–$C_4$ lower alkyl as said substituent may be linear or branched, and is exemplified by methyl, ethyl, n-propyl, isopropyl, n-butyl and isobutyl, with preference given to methyl, ethyl, n-propyl and isopropyl, and more preference given to methyl: the halogen atom is exemplified by chlorine, bromine, fluorine and iodine atoms, with preference given to chlorine and fluorine atoms: $C_1$–$C_4$ lower alkoxy is exemplified by methoxy, ethoxy, n-propoxy, isopropoxy and n-butoxy, with preference given to methoxy and ethoxy, and more preference given to methoxy.

When the R' in —$(CH_2)$j-R', which is represented by R9 is an aromatic group, this aromatic group may have a substituent on the ring. The $C_1$–$C_4$ lower alkyl as said substituent may be linear or branched, and is exemplified by methyl, ethyl, n-propyl, isopropyl, n-butyl and isobutyl, with preference given to methyl, ethyl, n-propyl and isopropyl, and more preference given to methyl: the halogen atom is exemplified by chlorine, bromine, fluorine and iodine atoms, with preference given to chlorine and fluorine atoms: $C_1$–$C_4$ lower alkoxy is exemplified by methoxy, ethoxy, n-propoxy, isopropoxy and n-butoxy, with preference given to methoxy and ethoxy, and more preference given to methoxy.

Examples of the aromatic group represented by R or R' include phenyl.

The $C_1$–$C_4$ lower alkoxy represented by R10 may be linear or branched, and is exemplified by methoxy, ethoxy, n-propoxy, isopropoxy and n-butoxy, with preference given to methoxy and ethoxy.

The compounds of the above-mentioned formulas [I] and [I'] of the present invention can be converted to pharmacologically acceptable salts as desired by a reaction with a suitable acid, or a base may be released from the salt produced.

The acids with which pharmacologically acceptable acid addition salts of the compounds of the above-mentioned formulas [I] and [I'] of the present invention are formed are exemplified by mineral acids such as hydrochloric acid, hydrobromic acid, sulfuric acid, nitric acid and phosphoric acid and organic acids such as (lower)alkylsulfonic acids (e.g., methanesulfonic acid, trifluoromethanesulfonic acid and ethanesulfonic acid), arylsulfonic acid (e.g., benzenesulfonic acid), acetic acid, maleic acid, fumaric acid, citric acid, malic acid, oxalic acid, lactic acid and tartaric acid. The reaction for forming a salt is readily carried out using a conventional method.

Each substituent in the formula [I] is preferably as follows.

R1 is H, halogen atom, —OH or $C_1$–$C_4$ lower alkoxy, R2 is H or —$NH_2$, R4 is H, halogen atom, —$NH_2$, —CN, —CHO, —$CH_2OH$ or —CH═N—OH, R5 is H and i is an integer of 1 to 3.

Each substituent in the formula [I'] is preferably as follows.

R3' is a group selected from the following (a) to (c):

(a)

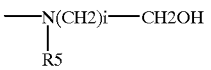

(b)

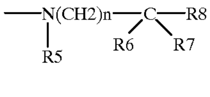

(c)

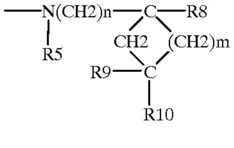

wherein R4 is H, halogen atom, —$NH_2$, —CN, —CHO, —$CH_2OH$ or —CH═N—OH, R5 is H, R6 and R7 are the same or different and each is $C_1$–$C_4$ lower alkyl, R8 is —OH, $C_1$–$C_4$ hydroxy(lower)alkyl or —$CH_2OC(O)CH_3$, R9 is H, —OH, $C_1$–$C_4$ lower alkyl, $C_1$–$C_4$ hydroxy(lower) alkyl, $C_1$–$C_4$ lower alkoxy, —$O(CH_2)$k-R where R is phenyl optionally having a substituent, and k is an integer of 0 to 4, or —$(CH_2)$j-R' where R' is an optionally substituted phenyl and j is an integer of 0 to 6, more preferably an integer of 0 to 4, R10 is H or $C_1$–$C_4$ lower alkoxy, i is an integer of 1 to 3, n is an integer of 1 to 4 (more preferably 1 or 2) and m is an integer of 0 to 4 (more preferably 1 or 2).

Of the compounds of the formula [I'], the compound wherein R3' has the formula (a), R5 is H and i is an integer of 1 to 3, and the compound wherein R3' has the formula (b) or (c), R5 is H, R8 is hydroxymethyl, n is an integer of 1 to 4 and m is an integer of 0 to 2 have superior anti-rotaviral action and are preferable compounds.

The novel pyrimidine compound of the above-mentioned formula [I] of the present invention can be produced by various methods. For example, the following methods produce the compound.

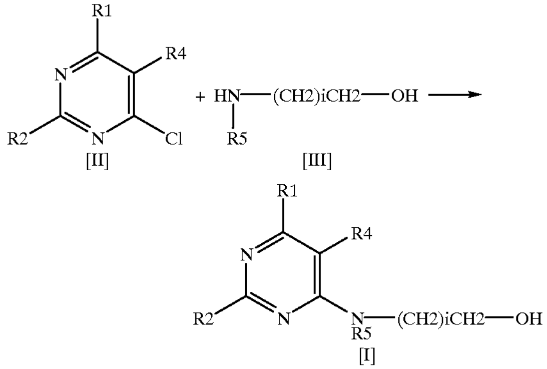

[II] [III] [I]

wherein R1, R2, R4, R5 and i are as defined above.

Production Method

A pyrimidine compound having the structure of the formula [II] is reacted with an amine compound of the formula [III] without solvent or in a solvent in the presence of a base as a dehydrohalogenating agent (deacidifying agent) to give a compound of the formula [I].

The organic solvent to be used in the present method may be any as long as it does not interfere with the reaction, and is exemplified by alcohol solvents such as methanol, ethanol, isopropanol and n-butanol, polar solvents such as tetrahydrofuran, dioxane, acetone, acetonitrile, N,N-dimethylformamide and dimethyl sulfoxide and nonpolar solvents such as benzene, toluene, xylene and chloroform. The reaction proceeds from under cooling to the boiling point of the solvent. The, time of reaction is 1 to 8 hours, preferably 3 to 8 hours.

A base which is a dehydrohalogenating agent (deacidifying agent) is used as a condensing agent, which is exemplified by potassium carbonate, sodium carbonate, potassium hydrogencarbonate, sodium hydrogencarbonate, pyridine, triethylamine and sodium hydride.

The pyrimidine compound of the above-mentioned formula [I'] of the present invention can be produced by various methods. For example, the following methods produce the compound.

Method A
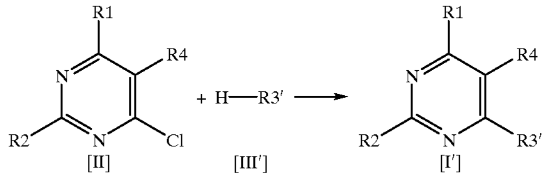
[II] [III'] [I']
wherein R1, R2, R3' and R4 are as defined above, and the compound of the formula [III'] is selected from the compounds of the following formulas [III-I] to [III-IV]:
[III-I]
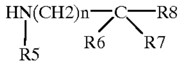
[III-II]
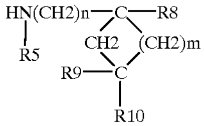
[III-III]
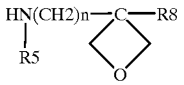
[III-IV]
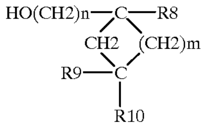
wherein R5, R6, R7, R8, R9, R10, n and m are as defined above.
Method B
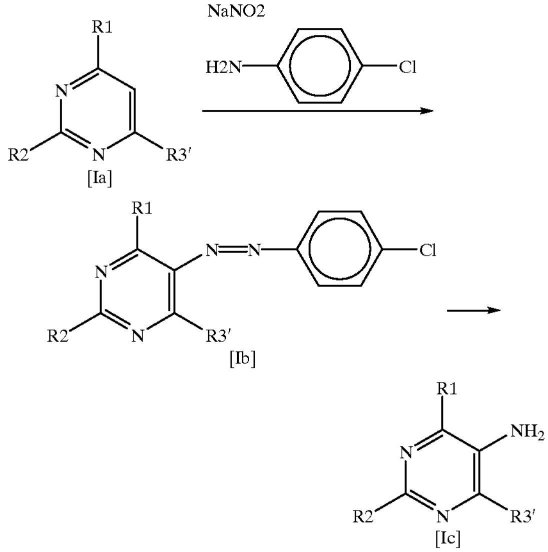
[Ia] [Ib] [Ic]
Method C-1
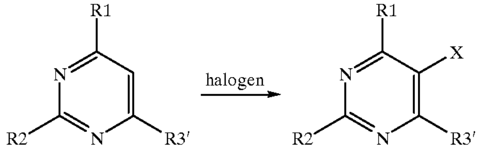
[Ia] [Id]
-continued
Method C-2
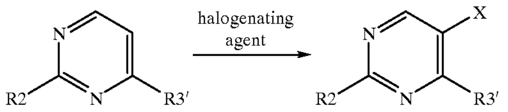
[Ie] [If]
Method D-1
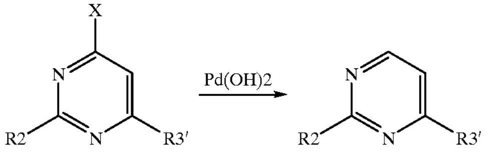
[Ig] [Ih]
Method D-2
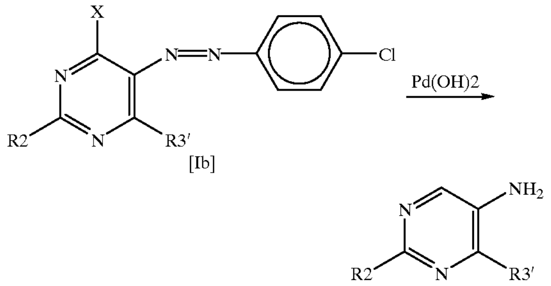
[Ib] [Ii]
Method D-3
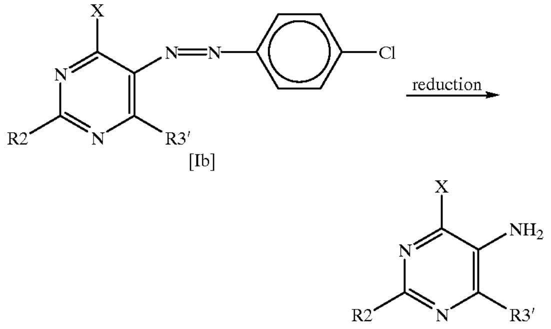
[Ib] [Ij]
Method E
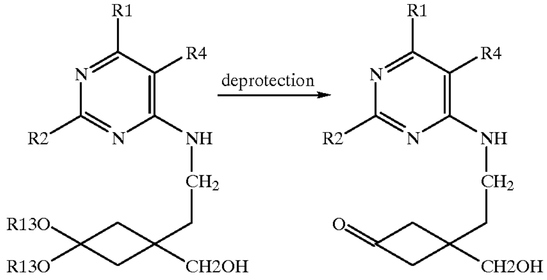
[Ik] [Il]
Method F
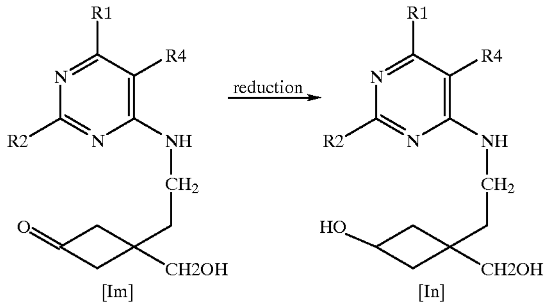
[Im] [In]

-continued

Method G

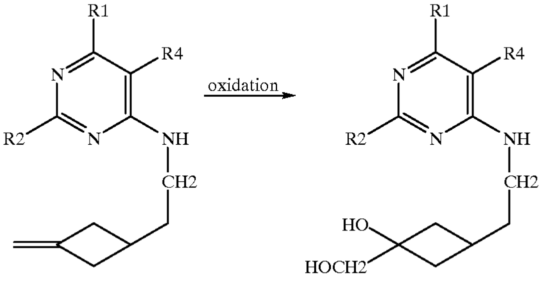

[Io] [Ip]

Method H

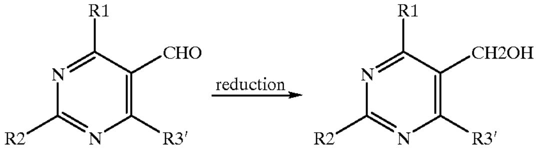

[Iq] [Ir]

Method I-1

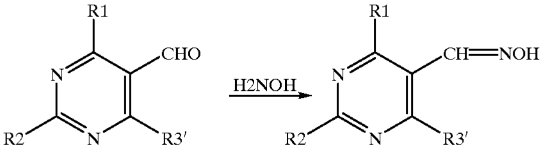

[Iq] [Is]

Method I-2

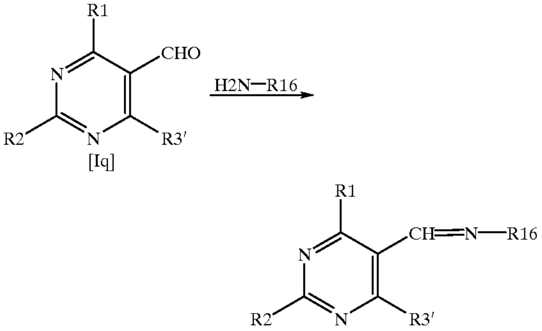

[Iq] [Iu]

Method J

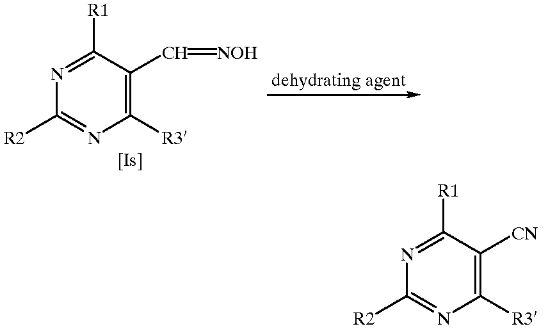

[Is] [It]

In the above formulas, R1, R2, R3' and R4 are as defined above, X is halogen atom such as bromine, chlorine, iodine and fluorine atoms, R13 is a carbonyl protecting group such as dialkylacetal and cyclic acetal and R16 is $C_1$–$C_4$ lower alkyl or $C_1$–$C_4$ lower alkoxy.

Method A relates to the production of compound of the formula [I']. According to Method A, a pyrimidine compound of the formula [II] is reacted with an amine compound of the formula $[III_{-I}]$, $[III_{-II}]$ or $[III_{-III}]$, or an alcohol compound of the formula $[III_{-IV}]$ without solvent or in a solvent in the presence of a condensing agent to give a compound [I'].

The organic solvent to be used in the present method may be any as long as it does not interfere with the reaction and is exemplified by alcohol solvents such as methanol, ethanol, isopropanol and n-butanol, polar solvents such as tetrahydrofuran, dioxane, acetone, acetonitrile, N,N-dimethylformamide and dimethyl sulfoxide and nonpolar solvents such as benzene, toluene, xylene and chloroform. The reaction proceeds from under cooling to the boiling point of the solvent. The time of reaction is 1 to 7 hours.

A base which is a dehydrohalogenating agent (deacidifying agent) is used as a condensing agent, which is exemplified by potassium carbonate, sodium carbonate, potassium hydrogencarbonate, sodium hydrogencarbonate, pyridine, triethylamine and sodium hydride.

Method B relates to the production of compound [Ic] wherein R4 is amino, from among the compounds of the above-mentioned formula [I']. As the first step, a mixture of a pyrimidine compound of the formula [Ia], p-chloroaniline and sodium nitrite is subjected to diazo-coupling reaction in an aqueous acidic solution of hydrochloric acid and the like at about 0° C. to give a compound wherein p-chlorophenylazo group has been introduced into the 5-position of the pyrimidine ring of the formula [Ib], and in the second step, the diazo compound of the formula [Ib] is subjected to reduction using zinc-acetic acid to give a compound [Ic].

According to Method C, a pyrimidine compound of the formula [Ia] or [Ie] is reacted with a halogenating agent to give a compound [Id] or [If] having halogen at the 5-position of the pyrimidine ring.

For the reaction, a pyrimidine compound of the formula [Ia] or [Ie] is reacted with a halogenating agent in a solvent. The halogenating agent to be used in the present production method may be, for example, chlorine, bromine, iodine, N-chlorosuccinimide, N-bromosuccinimide or N-iodosuccinimide.

The solvent to be used in the present production method may be any as long as it does not interfere with the reaction and is exemplified by polar solvents such as methanol, ethanol, isopropanol, acetic acid and N,N-dimethylformamide, benzene solvents such as benzene, toluene and xylene, and aprotic solvents such as chloroform, dichloromethane, carbon tetrachloride, ethyl ether, isopropyl ether, tetrahydrofuran and dioxane. The reaction proceeds from under cooling to the boiling point of the solvent.

Method D relates to the production of compounds of the above-mentioned formulas [Ih], [Ii] and [Ij].

According to Method D, a pyrimidine compound of the formula [Ib] or [Ig] is reduced, whereby dehalogenation and reduction of diazonium salt are simultaneously or separately carried out to give pyrimidine compounds of the formulas [Ih], [Ii] and [Ij]. The reducing agent to be used in Method D-1 and Method D-2 is preferably palladium hydroxide and this reaction can be processed using a conventional method. The reducing agent to be used in Method D-3 is preferably zinc-acetic acid and this reaction can be processed using a conventional method.

Method E relates to the production of compound of the above-mentioned formula [Il].

That is, a 2,5,6-substituted-4-(1-hydroxymethyl-3,3-dialkylacetal(or cyclic alkylacetal)cycloalkylmethylamino) pyrimidine compound of the formula [Ik] is treated with an acid by a conventional method to give a pyrimidine compound of the formula [Il]. In this production method, the acid to be used may be a single acid or a mixed acid of inorganic acids such as hydrochloric acid, sulfuric acid and phosphoric acid or organic acids such as formic acid, oxalic acid and acetic acid.

Method F relates to the production of compound of the above-mentioned formula [In].

A pyrimidine compound of the formula [Im] is reduced to give a pyrimidine compound of the formula [In]. The reducing agent to be used in the instant production method may be any as long as it is capable of reducing carbonyl group and the reduction can be carried out using a conventional method.

Method G relates to the production of compound of the above-mentioned formula [Ip].

A pyrimidine compound of the formula [Io] is oxidized to give a pyrimidine compound of the formula [Ip]. The oxidizing agent to be used in the instant production method may be, for example, osmium tetraoxide or a combination of osmium tetraoxide and a co-oxidizing agent, with preference given to osmium tetraoxide, which can be treated using a conventional method.

Method H relates to the production of compound of the above-mentioned formula [Ir].

A pyrimidine compound of the formula [Iq] is reduced to give a pyrimidine compound of the formula [Ir]. The reducing agent to be used in the instant production method may be any as long as it is capable of reducing formyl group and the reduction can be carried out using a conventional method.

Method I relates to the production of compound of the above-mentioned formula [Is] or [Iu].

A pyrimidine compound of the formula [Iq] is reacted with hydroxylamine or an amine compound of the formula: H2N—R16 in a solvent or without solvent to give a pyrimidine compound of the formula [Is] or [Iu].

The organic solvent to be used for reduction in the present method may be any as long as it does not interfere with the reaction and is exemplified by alcohol solvents such as methanol, ethanol, isopropanol and n-butanol, polar solvents such as tetrahydrofuran, dioxane, acetone, acetonitrile, N,N-dimethylformamide and dimethyl sulfoxide and nonpolar solvents such as benzene, toluene, xylene and chloroform. The reaction proceeds from room temperature to the boiling point of the solvent.

Method J relates to the production of compound of the formula [It].

A compound of the formula [I] wherein R4 is —CH═NOH is dehydrated in the presence of a dehydrating agent to give a pyrimidine compound of the formula [It].

The dehydrating agent to be used in the present invention may be, for example, acetic anhydride, acetic anhydride-sodium acetate, thionyl chloride, phosphorus pentaoxide, phosphorus pentachloride or benzoyl chloride.

Synthesis of intermediates

Of the compounds of the above-mentioned formulas [III$_{-I}$], [III$_{-II}$], [III$_{-III}$] and [III$_{-IV}$] which are used as intermediates in the instant production method, some are known compounds, and compound [III$_{-I}$] can be produced using the method described in U.S. Pat. No. 2,618,658, compound [III$_{-II}$] can be produced using the method described in Bull, Soc, Chim, France, 1965, 204, compound [III$_{-III}$] can be produced using the method described in UK Patent No. 1,169,027 and compound [III$_{-IV}$] can be produced using the method described in Zhur, Obshchei, Khim, 23, 1994(1953).

Of the intermediate compounds of the above-mentioned formula [III$_{-II}$], an amine compound of the formula [III$_{-II}$']

[III$_{-II}$']

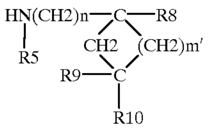

wherein m' is an integer of 1 to 4, R5, R8, R9, R10 and n are as defined above, the cycloalkyl ring in the formula may have a double bond at an optional position in the ring, exclusive of a compound where R5, R9 and R10 are hydrogen atoms, R8 is hydroxymethyl, m' is an integer of 1 to 4, n is 1, and cycloalkyl ring is a saturated ring, and a compound where n=O and R8=H, can be produced by the following methods.

An intermediate amine compound of the formula [III$_{-II}$] can be produced according to the following methods.

Method K

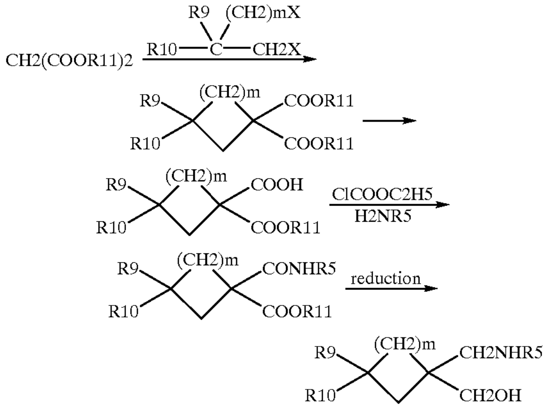

[III$_{-II}$a]

Method L

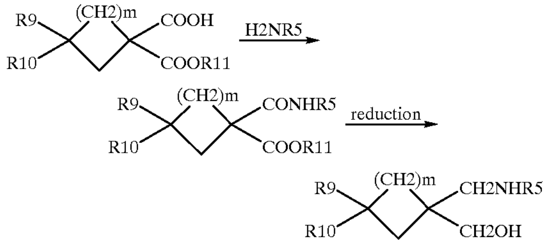

[III$_{-II}$a]

Method M

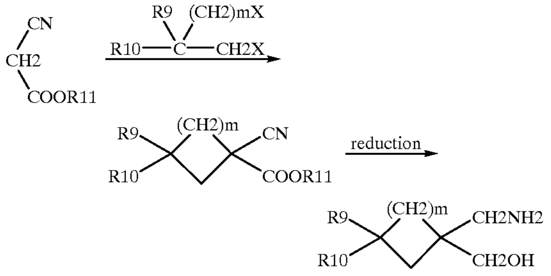

[III$_{-II}$b]

Method N

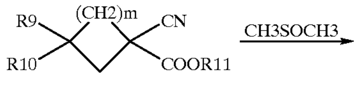

-continued

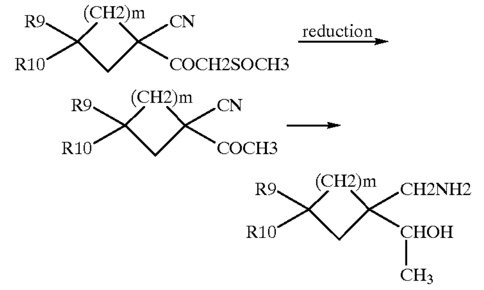

[III$_{-II}$c]

Method P

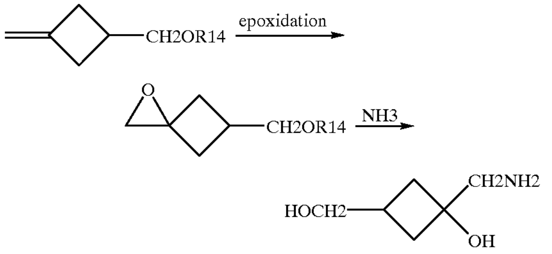

[III$_{-II}$d]

Method Q

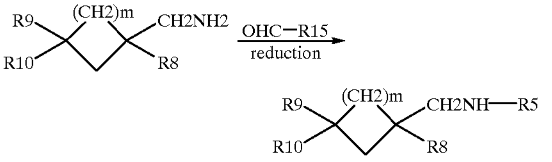

[III$_{-II}$e]

Method R

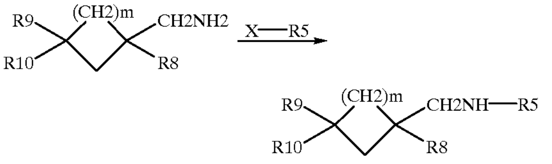

[III$_{-II}$e]

Method S

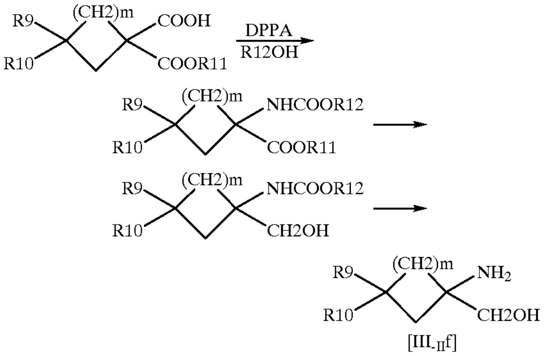

[III$_{-II}$f]

In the above formulas, R5, R8, R9, R10, X and m are as defined above, R11 is alkyl, preferably $C_1$–$C_4$ alkyl such as methyl and ethyl, R12 is alkyl, preferably $C_1$–$C_4$ alkyl such as methyl and ethyl, or benzyl, R14 is acyl such as benzoyl, and R15 is H or $C_1$–$C_3$ alkyl. In the formula [III$_{-II}$e], R5 is $C_1$–$C_4$ alkyl.

Method K relates to the production of compound of the formula [III$_{-II}$a].

Step 1

A dialkyl malonate is subjected to ring-closing reaction in the presence of β-substituted-α,ω-dihaloalkane and alcoholate to give a dialkyl ester of 3-substituted-1,1-cycloalkanedicarboxylic acid.

Step 2

The dialkyl ester of 3-substituted-1,1-cycloalkanedicarboxylic acid is subjected to selective hydrolysis in the presence of an alkali to give an alkyl ester of 3-substituted cycloalkane-1,1-dicarboxylic acid.

Step 3

The alkyl ester of 3-substituted cycloalkane-1,1-dicarboxylic acid is reacted with ethyl chlorocarbonate in a non-polar solvent in the presence of a base, and then reacted with ammonia or an amine to give an alkyl ester of 3-substituted-1-carbamoyl-1-cycloalkylcarboxylic acid.

Step 4

The obtained alkyl ester of 3-substituted-1-carbamoyl-1-cycloalkylcarboxylic acid is reduced by a conventional method to give 3-substituted-1-hydroxymethyl-1-cycloalkylmethylamine compound of the formula [III$_{-II}$a].

For the reaction, the alcoholate to be used in Step 1 may be, for example, sodium methylate, sodium ethylate or potassium tert-butylate; the temperature of reaction is from under cooling to the boiling point of the solvent; and the reaction time is 1 to 5 hours. Examples of the alkali to be used in Step 2 include aqueous solutions of sodium hydroxide, potassium hydroxide, sodium carbonate, potassium carbonate, sodium hydrogencarbonate and the like, and aqueous alcohol solutions of sodium hydroxide and potassium hydroxide. The temperature of reaction is from under cooling to the boiling point of the solvent, preferably room temperature, and the reaction time is 1 to 72 hours. The nonpolar solvent to be used in Step 3 includes, for example, benzene, toluene, xylene and chloroform, and the base used therein includes, for example, triethylamine and dimethylaniline. The temperature of reaction is from 10° C. to the boiling point of the solvent. The reducing agent to be used in Step 4 may be, for example, $LiAlH_4$, which can be treated using a conventional method. The reaction solvent includes, for example, tetrahydrofuran, ethyl ether, dioxane and pyridine. The temperature of reaction is from 0° C. to the boiling point of the solvent, and the reaction time is 1 to 5 hours.

Method L relates to the production of compound of the formula [III$_{-II}$a].

Step 1

An alkyl ester of 3-substituted-1-carboxy-1-cycloalkylcarboxylic acid is reacted with a halogenoacylating agent in a nonpolar solvent or without solvent, and then reacted with ammonia or an amine in the presence of a base to give an alkyl ester of 3-substituted-1-carbamoyl-1-cycloalkylcarboxylic acid.

Step 2

The obtained alkyl ester of 3-substituted-1-carbamoyl-1-cycloalkylcarboxylic acid is reduced by a conventional method to give a 3-substituted-1-hydroxymethyl-1-cycloalkylmethylamine compound of the formula [III$_{-II}$a].

The solvent to be used in Step 1 is exemplified by nonpolar solvents such as benzene, toluene, xylene and chloroform and halogenoacylating agent is exemplified by thionyl chloride, phosphorus oxychloride, phosphorus pentachloride. Examples of the base include triethylamine and dimethylaniline. The temperature of reaction is from 10° C. to the boiling point of the solvent. The reducing agent to be used in Step 2 includes $LiAlH_4$ which can be treated by a conventional method. The reaction solvent and reaction conditions are to be referred to those shown in Step 4 of Method K.

Method M relates to the production of compound of the formula [$III_{-II}$b].

Step 1

An alkyl cyanoacetate is subjected to ring-closing reaction in the presence of β-substituted-α,ω-dihaloalkane and alcoholate to give an alkyl ester of 3-substituted-1-cyano-1-cycloalkylcarboxylic acid.

Step 2

The obtained alkyl ester of 3-substituted-1-cyano-1-cycloalkylcarboxylic acid is reduced by a conventional method to give a 3-substituted-1-hydroxymethyl-1-methylaminocycloalkane compound of the formula [$III_{-II}$b].

The alcoholate to be used in Step 1 includes, for example, sodium methylate, sodium ethylate, potassium tert-butylate and the like. The temperature of reaction is from under cooling to the boiling point of the solvent, and the reaction time is 1 to 5 hours. The reducing agent to be used in Step 2 includes $LiAlH_4$, $B_2H_6$, $NaBH_4$ and the like, and the catalyst may be, for example, aluminum chloride as a Lewis acid or cobalt chloride as a transition metal salt, which can be treated by a conventional method. For example, a catalyst is used in an amount of 0.1–1.5 equivalents. The reaction solvent is exemplified by tetrahydrofuran, ethyl ether, dioxane and the like. The temperature of reaction is from under cooling to the boiling point of the solvent, and the reaction time is 1 to 5 hours.

Method N relates to the production of compound of the above-mentioned formula [$III_{-II}$c].

Step 1

An alkyl ester of 3-substituted-1-cyano-1-cycloalkylcarboxylic acid is reacted with alkaline metal hydride and dimethyl sulfoxide in an anhydrous solvent to give a 3-substituted-1-cyano-1-methylsulfinylmethylcarbonylcycloalkane compound.

Step 2

The obtained 3-substituted-1-cyano-1-methylsulfinylmethylcarbonylcycloalkane compound is reduced with metal amalgam in a solvent to give a 3-substituted-1-cyano-1-acetylcycloalkane compound.

Step 3

The obtained 3-substituted-1-cyano-1-acetylcycloalkane compound is reduced by a conventional method to give a 3-substituted-1-(α-alkyl)-hydroxymethyl-1-cycloalkylmethylamine compound of the formula [$III_{-II}$c].

The alkaline metal hydride to be used in Step 1 may be, for example, sodium hydride or potassium hydride and the anhydrous solvent is exemplified by tetrahydrofuran, ethyl ether, dioxane, benzene, toluene and xylene. The temperature of reaction is from 10° C. to 50° C., and the reaction time is 0.5 to 3 hours. The anhydrous solvent to be used in Step 2 is exemplified by tetrahydrofuran, ethyl ether, dioxane, benzene, toluene, xylene, chloroform, methylene chloride and dichloroethane. The metal amalgam to be used includes, for example, aluminum amalgam. The temperature of reaction is from room temperature to 80° C., and the reaction time is 1 to 5 hours. The reducing agent to be used in Step 3 includes $LiAlH_4$ and the like, which can be treated by a conventional method. The reaction solvent and reaction conditions are to be referred to those shown in Step 4 of Method K.

Method P relates to the production of compound of the formula [$III_{-II}$d].

Step 1

A 1-acyloxymethyl-3-methylenecycloalkane is reacted with a peroxide in an anhydrous nonpolar solvent to give a 1-acyloxymethyl-3-cycloalkylmethylene oxide.

Step 2

The obtained 1-acyloxymethyl-3-cycloalkylmethylene oxide is reacted with saturated alcoholic ammonia to give a 1-hydroxymethyl-3-hydroxy-3-cycloalkylmethylamine compound of the formula [$III_{-II}$].

For example, the 1-acyloxymethyl-3-methylenecycloalkane which is the starting material in Step 1 can be produced in the following manner. That is, 1-ethoxycarbonyl-3-methylenecyclobutane is reduced to give 1-hydroxymethyl-3-methylenecyclobutane, which is reacted with acyl halide in the presence of a base to protect hydroxyl group, whereby 1 -acyloxymethyl-3-methylenecyclobutane can be obtained.

The anhydrous nonpolar solvent to be used in Step 1 includes, for example, acetonitrile, tetrahydrofuran, ethyl ether, dioxane, benzene, toluene, xylene, chloroform, methylene chloride and dichloroethane, and, peroxide includes, for example, perbenzoic acid and m-chloroperbenzoic acid. The temperature of reaction is from room temperature to the boiling point of the solvent, and the reaction time is 0.5 to 12 hours. The saturated alcoholic ammonia to be used in Step 2 is exemplified by saturated ammonia-methanol solution and the reaction proceeds in said solution. The temperature of reaction is from under cooling to the boiling point of the solvent, and the reaction time is 0.5 to 5 hours.

Method Q relates to the production of compound of the above-mentioned formula [$III_{-II}$e].

A 1,3-substituted-1-cycloalkylmethylamine compound is subjected to reductive alkylation of amino group wherein the compound is reacted with formaldehyde or alkylaldehyde in a solvent in the presence of a reducing agent such as $NaBH_3CN$ and $NaBH_4$ to give a compound of the formula [$III_{-II}$e]. The organic solvent to be used for reduction in the instant production method may be any as long as it does not interfere with the reaction and is exemplified by alcohol solvents such as methanol, ethanol, isopropanol and n-butanol. The temperature of reaction is from under cooling to the boiling point of the solvent, and the reaction time is 1 to 20 hours.

Method R relates to the production of compound of the above-mentioned formula [$III_{-II}$e].

A 1,3-substituted-1-cycloalkylmethylamine compound is reacted with alkyl halide in a solvent in the presence of base as a dehydrohalogenating agent to give a 1,3-substituted-cycloalkyl-1-(N-alkyl)methylamine compound of the formula [$III_{-II}$e].

The organic solvent to be used in the instant production method may be any as long as it does not interfere with the reaction and is exemplified by alcohol solvents such as methanol, ethanol, isopropanol and n-butanol, aprotic polar solvents such as acetone, acetonitrile, N,N-dimethylformamide and dimethyl sulfoxide, and aprotic nonpolar solvents such as benzene, toluene, xylene, chloroform, dichloromethane, carbon tetrachloride, ethyl ether, isopropyl ether, tetrahydrofuran and dioxane. The base to be used as a dehydrohalogenating agent may be, for example, potassium carbonate, sodium carbonate, potassium hydrogencarbonate, sodium hydrogencarbonate, pyridine or triethylamine. The temperature of reaction is from under cooling to the boiling point of the solvent, and the reaction time is 1 to 24 hours.

Method S relates to the production of compound of the above-mentioned formula [$III_{-II}$f].

Step 1

A 3-substituted-1-alkoxycarbonyl-1-cycloalkylcarboxylic acid is dissolved in a dry nonpolar solvent and subjected to reaction under heating (Curtius rearrangement) with diphenylphosphoryl azide (DPPA) in the presence of a base and then reacted under heating with an alcohol (alkyl alcohol or benzyl alcohol) of the formula

R120H to give an alkyl(or benzyl) 3-substituted-1-alkoxycarbonyl-1-cycloalkylcarbamate.

Step 2

The alkoxycarbonyl group of the alkyl(or benzyl) 3-substituted-1-alkoxycarbonyl-1-cycloalkylcarbamate is reduced to give an alkyl(or benzyl) 3-substituted-1-hydroxymethyl-1-cycloalkylcarbamate.

Step 3

The alkyl(or benzyl) 3-substituted-1-hydroxymethyl-1-cycloalkylcarbamate is hydrogenolyzed or decomposed with an acid to give a 3-substituted-1-hydroxymethyl-1-cycloalkylamine compound of the formula [$III_{-II}$f].

The nonpolar solvent to be used in Step 1 is exemplified by benzene, toluene, xylene, ethyl ether, isopropyl ether, tetrahydrofuran and dioxane and the base is exemplified by triethylamine, dimethylaniline and the like. The temperature of the heating reaction is up to the boiling point of the solvent, and the reaction time is 1 to 15 hours.

The reducing agent to be used in Step 2 includes $LiAlH_4$, $LiBH_4$ and the like, which can be treated by a conventional method. The reaction solvent may be, for example, tetrahydrofuran, ethyl ether, dioxane and the like. The temperature of reaction is from under cooling to the boiling point of the solvent, and the reaction time is 0.5 to 5 hours.

In the hydrogenolysis to be used in Step 3, a palladium catalyst is used and hydrogen is added at normal pressure. The reaction solvent may be, for example, methanol, ethanol or propanol and the temperature of reaction is from room temperature to the boiling point of the solvent. Examples of the palladium catalyst include palladium hydroxide, palladium chloride and the like, which is used in 0.05–1 equivalent. The reaction time is 1 to 5 hours. The acid to be used in acid decomposition includes, for example, phosphonium iodide, acetic acid and a mixed acid of hydrobromide or hydrogen chloride in acetic acid. The reaction solvent may be, for example, water or alcohol. The temperature of reaction is from room temperature to the boiling point of the solvent and the reaction time is 1 to 5 hours.

The pyrimidine compound of the formula [I'] and pharmacologically acceptable salts thereof of the present invention have anti-viral activity, particularly, anti-rotaviral activity, and are useful as anti-rotavirus agents or agents for the prophylaxis and treatment of rotaviral diseases. In particular, the pyrimidine compound of the formula [I] and pharmacologically acceptable salts thereof of the present invention are novel compounds which are useful as anti-rotavirus agents or agents for the prophylaxis and treatment of rotaviral diseases.

The anti-rotavirus agents or agents for the prophylaxis and treatment of rotaviral diseases of the present invention contain at least one pyrimidine compound of the formula [I'] or a pharmacologically acceptable salt thereof as an active ingredient. Therefore, they may contain two or more pyrimidine compounds of the formula [I'] or pharmacologically acceptable salts thereof.

The rotaviral diseases are caused by infection with rotavirus, which specifically manifest as symptoms such as diarrhea, particularly infant diarrhea, emesis and dehydration, which are caused by infection with rotavirus.

The compound of the present invention is admixed with an appropriate carrier for preparations and administered as a pharmaceutical composition. The dosage form may be oral or parenteral, wherein the oral preparation includes tablets, capsules, powders, fine particles, granules, liquids and syrups, and parenteral preparation includes injections and suppositories. These preparations can contain pharmacologically and pharmaceutically acceptable additives such as excipients, disintegrators, disintegration aids, binders, lubricants, coating agents and pigments.

Oral agents may contain glucose, lactose, D-mannitol, starch, crystalline cellulose and the like as excipients, carboxymethylcellulose, starch, carboxymethylcellulose calcium and the like as disintegrators and disintegration aids, hydroxypropylcellulose, hydroxymethylcellulose, polyvinylpyrrolidone, gelatin and the like as binders, magnesium stearate, talc and the like as lubricants, and hydroxypropylmethylcellulose, sucrose, titanium oxide and the like as coating agents. Injections may contain conventional ingredients for preparations such as distilled water for injection, physiological saline, propylene glycol and the like as solvents and solubilizers, glucose, sodium chloride, D-mannitol, glycerol and the like as isotonizing agents, and inorganic acid, organic acid, inorganic base and organic base as pH adjusting agents.

While the dose of the compound of the present invention varies depending on the symptom, age and the like of patients to be treated and administration route, it is generally 0.1–1000 mg/kg/day.

The pharmaceutical composition of the present invention contains varying amounts of active ingredient depending on the form of preparation, and the content of the active ingredient is not particularly limited. It is generally 0.01–90 wt %, preferably 0.01–20 wt %, particularly preferably 0.1–10 wt %, of the total amount of the composition.

The present invention is described in more detail by way of Examples, Production Examples and Experimental Examples, which should not be construed as limiting the invention.

EXAMPLE 1

2-Amino-6-chloro-4-[(2-hydroxyethyl)amino]pyrimidine (compound No. 105)

To 2-hydroxyethylamine (2.6 g, 42.7 mmol) were added 2-amino-4,6-dichloropyrimidine (7.0 g, 42.7 mmol), ethanol (150 ml) and triethylamine (6.6 ml), and the mixture was refluxed for one day. The solvent was distilled away under reduced pressure and the residue was washed with water, which was followed by recrystallization from chloroform to give yellow prism crystals (4.8 g, 59.6%), m.p. 143–146° C. (chloroform).

EXAMPLE 2

2-Amino-6-chloro-4-[(2-hydroxyethyl)amino]pyrimidine hydrochloride (compound No. 106)

2-Amino-6-chloro-4-[(2-hydroxyethyl)amino]pyrimidine (0.5 g, 2.7 mmol) was dissolved in 20 ml of methanol, and 3 equivalents of 14% HCl-methanol solution was carefully added under ice-cooling. The mixture was warmed to room temperature and the solvent was distilled away to give white crystals (0.64 g, 92.9%), m.p. 173–176° C. (ether).

EXAMPLE 3

2-Amino-6-chloro-4-[(3-hydroxypropyl)amino]pyrimidine (compound No. 107)

To 3-hydroxypropylamine (7.51 g, 0.1 mol) were added 2-amino-4,6-dichloropyrimidine (16.40 g, 0.1 mol), ethanol (350 ml) and triethylamine (11.13 ml), and the mixture was refluxed for one day. The solvent was distilled away under reduced pressure. The residue was dissolved in ethyl acetate, washed with water and dried over anhydrous magnesium sulfate. The solvent was distilled away to give white crystals (20.0 g, 98.7%), m.p. 160–163° C. (ethanol).

EXAMPLE 4

2-Amino-6-chloro-4-[(3-hydroxypropyl)amino]pyrimidine hydrochloride (compound No. 108)

2-Amino-6-chloro-4-[(3-hydroxypropyl)amino]pyrimidine (2 g, 0.01 mol) was dissolved in 20 ml of methanol, and 3 equivalents of 14% HCl-methanol solution was carefully added under ice-cooling. The mixture was warmed to room temperature and the solvent was distilled away. The residue was recrystallized from chloroform-ethyl acetate to give white crystals (1.9 g, 79.5%), m.p. 170–180° C. (chloroform-ethyl acetate).

EXAMPLE 5

2-Amino-6-chloro-4-[(4-hydroxybutyl)amino]pyrimidine (compound No. 109)

To 4-hydroxybutylamine (10.0 g, 0.112 mol) were added 2-amino-4,6-dichloropyrimidine (16.73 g, 0.102 mol), ethanol (400 ml) and triethylamine (24.9 ml), and the mixture was refluxed for one day. The solvent was distilled away under reduced pressure. The residue was dissolved in ethyl acetate, washed with water and dried over anhydrous magnesium sulfate. The solvent was distilled away and the residue was purified by silica gel column chromatography (chloroform:methanol=20:1, later 10:1) to give colorless prism crystals (18.7 g, 84.7%), m.p. 139–141° C. (methanol).

EXAMPLE 6

2-Amino-6-chloro-4-[(4-hydroxybutyl)amino]pyrimidine hydrochloride (compound No. 110)

2-Amino-6-chloro-4-[(4-hydroxybutyl)amino]pyrimidine (0.8 g, 3.69 mmol) was dissolved in 10 ml of methanol, and 3 equivalents of 14% HCl-methanol solution was carefully added under ice-cooling. The mixture was warmed to room temperature and the solvent was distilled away to give white crystals (0.6 g, 64.1%), m.p. 143–146° C. (ether).

EXAMPLE 7

6-Chloro-2,5-diamino-4-[(2-hydroxyethyl)amino]pyrimidine (compound No. 111)

Step 1; 2-Amino-6-chloro-5-[(p-chlorophenyl)azo]-4-[(2-hydroxyethyl)amino]pyrimidine 2-Amino-6-chloro-4-[(2-hydroxyethyl)amino]pyrimidine (2.0 g, 10.64 mmol) was dissolved in a mixture of sodium acetate (12.84 g), acetic acid (53.2 ml) and water (53 ml), and a cold p-chlorobenzenediazonium chloride solution prepared by dissolving p-chloroaniline (1.76 g, 13.83 mmol) in water (11 ml) and conc. hydrochloric acid (3.26 ml) at room temperature and dropwise adding thereto sodium nitrite (1.13 g, 16.39 mmol) dissolved in water (11 ml) at 2–3° C. was dropwise added. The mixture was stirred for one day. The resulting crystals were collected by filtration and washed with water to give orange-yellow crystals (3.03 g, 87.2%).

Step 2; 6-Chloro-2,5-diamino-4-[(2-hydroxyethyl)amino]pyrimidine

To 2-amino-6-chloro-5-[(p-chlorophenyl)azo]-4-[(2-hydroxyethyl)amino]pyrimidine (3.0 g, 9.2 mmol) were added ethanol (76.0 ml), water (76.0 ml) and acetic acid (8.0 ml), and the mixture was heated to 70° C. A zinc powder (7.52 g) was added portionwise with stirring in a nitrogen stream and the mixture was stirred at the same temperature for 1.5 hours to give a solution. The reaction mixture was filtered and the solvent of the filtrate was distilled away under reduced pressure. Water was added to the residue and the mixture was extracted with chloroform, washed with water and dried over anhydrous magnesium sulfate. The solvent was distilled away under reduced pressure and the residue was purified by silica gel column chromatography (chloroform:methanol=20:1) to give pale-brown crystals (0.34 g, 18.3%), m.p. 164–167° C.

EXAMPLE 8

6-Chloro-2,5-diamino-4-[(2-hydroxyethyl)amino]pyrimidine dihydrochloride (compound No. 112)

6-Chloro-2,5-diamino-4-[(2-hydroxyethyl)amino]pyrimidine (0.495 g, 2.44 mmol) was dissolved in 10 ml of methanol, and 3 equivalents of 14% HCl-methanol solution was carefully added under ice-cooling. The mixture was warmed to room temperature and the solvent was distilled away to give white crystals (0.48 g, 72.0%), m.p. 158–161° C. (ether).

EXAMPLE 9

6-Chloro-2,5-diamino-4-[(3-hydroxypropyl)amino]pyrimidine (compound No. 113)

Step 1; 2-Amino-6-chloro-5-[(p-chlorophenyl)azo]-4-[(3-hydroxypropyl)amino]pyrimidine 2-Amino-6-chloro-4-[(3-hydroxypropyl)amino]pyrimidine (10 g, 0.049 mol) was dissolved in a mixture of sodium acetate (98.7 g), acetic acid (246.7 ml) and water (200 ml), and a cold p-chlorobenzenediazonium chloride solution prepared by dissolving p-chloroaniline (6.94 g, 0.054 mol) in water (40 ml) and conc. hydrochloric acid (15.1 ml) at room temperature and dropwise adding thereto sodium nitrite (4.15 g, 0.059 mol) dissolved in water (40 ml) at 2–3° C. was dropwise added. The mixture was stirred for one day. The resulting crystals were collected by filtration and washed with water to give orange-yellow crystals (9.29 g, 58.9%), m.p. 225–267° C. (ethanol).

Step 2; 6-Chloro-2,5-diamino-4-[(3-hydroxypropyl)amino]pyrimidine

To 2-amino-6-chloro-5-[(p-chlorophenyl)azo]-4-[(3-hydroxypropyl)amino]pyrimidine (8.19 g, 0.024 mol) were added ethanol (208.7 ml), water (208.7 ml) and acetic acid (20.9 ml), and the mixture was heated to 70° C. A zinc powder (19.65 g) was added portionwise with stirring in a nitrogen stream and the mixture was stirred at the same temperature for 1.5 hours to give a solution. The reaction mixture was filtered and the solvent of the filtrate was distilled away under reduced pressure. Water was added to the residue and the mixture was extracted with chloroform, washed with water and dried over anhydrous magnesium sulfate. The solvent was distilled away under reduced pressure and the residue was purified by silica gel column chromatography (chloroform:methanol=20:1) to give pale-brown crystals (5.0 g, 95.7%), m.p. 119–120° C. (ethyl acetate).

EXAMPLE 10

6-Chloro-2,5-diamino-4-[(3-hydroxypropyl)amino]pyrimidine dihydrochloride (compound No. 114)

6-Chloro-2,5-diamino-4-[(3-hydroxypropyl)amino]pyrimidine (0.290 g, 1.0 mmol) was dissolved in 20 ml of methanol, and 3 equivalents of 14% HCl-methanol solution was carefully added under ice-cooling. The mixture was warmed to room temperature and the solvent was distilled away to give white crystals (0.26 g, 90.0%), m.p. 120–131° C. (ether).

EXAMPLE 11

6-Chloro-2,5-diamino-4-[(4-hydroxybutyl)amino]pyrimidine (compound No. 115)

Step 1; 2-Amino-6-chloro-5-[(p-chlorophenyl)azo]-4-[(4-hydroxybutyl)amino]pyrimidine 2-Amino-6-chloro-4-[(4-hydroxybutyl)amino]pyrimidine (10.7 g, 0.0493 mol) was dissolved in a mixture of sodium acetate (59.5 g), acetic acid (246.7 ml) and water (246.7 ml), and a cold p-chlorobenzenediazonium chloride solution prepared by dissolving p-chloroaniline (6.94 g, 0.0544 mol) in water (51.3 ml) and conc. hydrochloric acid (15.1 ml) at room temperature and dropwise adding thereto sodium nitrite (4.15 g, 0.0601 mol) dissolved in water (51.3 ml) at 2–3° C. was dropwise added. The mixture was stirred for one day. The resulting crystals were collected by filtration and washed with water to give orange-yellow crystals (11.27 g, 64.4%).

Step 2; 6-Chloro-2,5-diamino-4-[(4-hydroxybutyl)amino]pyrimidine

To 2-amino-6-chloro-5-[(p-chlorophenyl)azo]-4-[(4-hydroxybutyl)amino]pyrimidine (1.57 g, 4.42 mmol) were added ethanol (38.4 ml), water (38.4 ml) and acetic acid (3.84 ml), and the mixture was heated to 70° C. A zinc powder (3.61 g) was added portionwise with stirring in a nitrogen stream and the mixture was stirred at the same temperature for 1.5 hours to give a solution. The reaction mixture was filtered and the solvent of the filtrate was distilled away under reduced pressure. Water was added to the residue and the mixture was extracted with chloroform, washed with water and dried over anhydrous magnesium sulfate. The solvent was distilled away under reduced pressure and the residue was purified by silica gel column chromatography (chloroform:methanol=20:1) to give red-brown crystals (0.93 g, 90.9%), m.p. 58–62° C. (methanol).

EXAMPLE 12

6-Chloro-2,5-diamino-4-[(4-hydroxybutyl)amino]pyrimidine dihydrochloride (compound No. 116)

6-Chloro-2,5-diamino-4-[(4-hydroxybutyl)amino]pyrimidine (0.55 g, 2.37 mmol) was dissolved in 5 ml of methanol, and 3 equivalents of 14% HCl-methanol solution was carefully added under ice-cooling. The mixture was warmed to room temperature and the solvent was distilled away to give black-red crystals (0.54 g, 85.1%), m.p. 159–161° C. (ether).

PRODUCTION EXAMPLE OF COMPOUND OF FORMULA [I']

METHOD A

PRODUCTION EXAMPLE 1, METHOD A-1

2-Amino-6-chloro-4-[(3-hydroxy-2,2-dimethylpropyl)amino]pyrimidine (compound No. 20)

3-Hydroxy-2,2-dimethylpropylamine (2.5 g, 0.0243 mol) and 2-amino-4,6-dichloropyrimidine (4.0 g, 0.0243 mol) were dissolved in ethanol (100 ml). Triethylamine (5 ml) was added and the mixture was refluxed for one day. The solvent was distilled away under reduced pressure. The residue was washed with water, dried and recrystallized from chloroform-methanol to give colorless prism crystals (3.96 g, 70.7%), m.p. 203–207° C. (chloroform-methanol).

PRODUCTION EXAMPLE 2, METHOD A-2

2-Amino-6-chloro-4-[[(1-hydroxymethyl-1-cyclobutyl)methyl]amino]-pyrimidine (compound No. 35)

A mixture of 1-hydroxymethyl-1-cyclobutylmethylamine (5.75 g, 0.05 mol), 2-amino-4,6-dichloropyrimidine (8.20 g, 0.05 mol), ethanol (200 ml) and triethylamine (20 ml) was refluxed for one day. The solvent was distilled away under reduced pressure. The residue was washed with water, dried and recrystallized from acetone to give colorless prism crystals (11.2 g, 92.3%), m.p. 192–194° C. (acetone).

PRODUCTION EXAMPLE 3, METHOD A-3

2-Amino-6-chloro-4-[[(3-hydroxymethyloxetan-3-yl)methyl]amino]-pyrimidine (compound No. 26)

A mixture of 3-aminomethyl-3-hydroxymethyloxetane (1.17 g, 0.01 mol), 2-amino-4,6-dichloropyrimidine (1.64 g, 0.01 mol), ethanol (40 ml) and triethylamine (4 ml) was refluxed for one day. The solvent was distilled away under reduced pressure and ethyl acetate was added to the residue. The mixture was washed with water and dried over anhydrous magnesium sulfate. The solvent was distilled away under reduced pressure and the residue was purified by silica gel column chromatography (chloroform:methanol=20:1, later 10:1) to give colorless prism crystals (0.8 g, 32.8%), m.p. 185–186° C. (acetone).

PRODUCTION EXAMPLE 4, METHOD A-4

2-Amino-6-chloro-4-[(1-hydroxymethyl-1-cyclobutyl)methoxy]pyrimidine (compound No. 95)

60% Sodium hydride (0.4 g, 0.01 mol) was suspended in dry dioxane (40 ml) and dihydroxymethylcyclobutane (1.16 g, 0.01 mol) dissolved in dry dioxane (40 ml) was dropwise added thereto. The mixture was stirred at 60–70° C. for 30 minutes, and 2-amino-4,6-dichloropyrimidine (1.64 g, 0.01 mol) was added. The mixture was refluxed for 3 hours, and filtrated. The solvent in the filtrate was distilled away under reduced pressure and the residue was purified by silica gel column chromatography (chloroform:methanol=50:1) to give white crystals (1.24 g, 50.8%), m.p. 125–127° C. (acetone).

PRODUCTION EXAMPLE 5, METHOD A-5

2-Amino-6-chloro-4-[[(3-(2-phenylethyl)-1-hydroxymethyl-1-cyclobutyl)methyl]amino]-5-formylpyrimidine (compound No. 71)

1-Hydroxymethyl-3-(2-phenylethyl)-1-cyclobutylmethylamine (3.51 g, 0.016 mol) was dissolved in ethanol (60 ml), and 2-amino-4,6-dichloro-5-formylpyrimidine (3.07 g, 0.016 mol) and triethylamine (6 ml) were added, which was followed by reflux for 2 hours. The solvent was distilled away under reduced pressure and chloroform was added to the residue. The mixture was washed with water and dried over anhydrous magnesium sulfate. The solvent was distilled away under reduced pressure and the residue was purified by silica gel column chromatography (chloroform, later chloroform:methanol=100:1) to give pale-yellow crystals (2.4 g, 40.0%), m.p. 130–137° C. (ether).

PRODUCTION EXAMPLE 6, METHOD A-6

2-Amino-6-chloro-4-[[1-hydroxymethyl-1-(2-cyclopentenyl)methyl]-amino]pyrimidine (compound No. 50)

Diethyl malonate (121.5 ml, 0.8 mol) and cis-1,4-dichloro-2-butene (44.3 ml, 0.4 mol) were reacted in the same manner as described in Jour. Org. Chem., Vol. 27, 2395 (1962) to give a diester mixture A (46.0 g, 54.1%). To the diester mixture A (25.5 g, 0.12 mol) was added potassium hydroxide (7.9 g, 0.12 mol) dissolved in 90% ethanol, which was followed by hydrolysis at room temperature for 2 days. The solvent was distilled away under reduced pressure and the residue was acidified with hydrochloric acid and extracted with ether to give a monoester compound B (17.4 g, 78.8%). To the monoester compound B (17.4 g, 0.95 mol) were added triethylamine (13.2 ml, 0.095 mol) and ethyl chlorocarbonate (9.1 ml, 0.095 mol) under ice-cooling and the mixture was reacted with ammonia gas for 15 minutes to give an amide ester compound C (14.2 g, 81.8%). The amide ester compound C (3.66 g, 0.02 mol) was dissolved in dry tetrahydrofuran and reduced with $LiAlH_4$ (2.28 g, 0.06 mol) to give an amino alcohol mixture D (2.43 g, 95.5%).

To the amino alcohol compound D (1.27 g, 0.01 mol) were added 2-amino-4,6-dichloropyrimidine (1.64 g, 0.01 mol), ethanol (40 ml) and triethylamine (2.1 ml), and the mixture was refluxed for one day. The solvent was distilled away under reduced pressure. Ethyl acetate was added to the residue and the mixture was subjected to hot filtration. The solvent of the filtrate was distilled away under reduced pressure and the residue was isolated by silica gel column chromatography (chloroform:methanol=50:1) to give colorless prism crystals (0.86 g, 33.8%) of the objective compound (compound No. 50), m.p. 201–203° C. (acetone).

PRODUCTION EXAMPLE 7, METHOD A-7

2-Amino-6-chloro-4-{[1-hydroxymethyl-1-[2-(1-hydroxyethyl)cyclopropyl]methyl]amino}pyrimidine (compound No. 34) and 2-amino-6-chloro- 4-[[1-hydroxymethyl-1-(3-hydroxycyclopentyl)methyl]amino]pyrimidine (compound No. 51)

The amide ester mixture C (3.66 g, 0.02 mol) obtained in Production Example 6 was dissolved in dichloromethane (15 ml), and m-chloroperbenzoic acid (4.31 g, 0.02 mol) dissolved in dichloromethane (40 ml) was added, which was followed by stirring at room temperature for 3 days. By a treatment using a conventional method gave epoxy compound E. Without purification, this compound was reduced using $LiAlH_4$ (2.28 g, 0.06 mol) in dry tetrahydrofuran as a solvent to give an aminodiol mixture F (2.1 g, 72.4%).

To the aminodiol mixture F (2.03 g, 0.014 mol) were added 2-amino-4,6-dichloropyrimidine (2.3 g, 0.014 mol), ethanol (55 ml) and triethylamine (5.5 ml), and the mixture was refluxed for one day. The solvent was distilled away under reduced pressure and chloroform was added to the residue to filter off insoluble matters. The filtrate was purified by silica gel column chromatography (chloroform:methanol=20:1) to give colorless prism crystals (0.82 g, 21.5%) of the objective compound (compound No. 34), m.p. 169–171° C. (acetone), in fractions 52–71. In addition, colorless prism crystals (0.26 g, 6.8%) of the objective compound (compound No. 51), m.p. 188–190° C. (acetone) were obtained, in fractions 90–132.

PRODUCTION EXAMPLE 8, METHOD A-8

2-Amino-6-chloro-4-[(3-benzoyloxymethyl-1-hydroxy-1-cyclobutyl)methoxy]pyrimidine (compound No. 91) and 2-amino-6-chloro-4-[(3-hydroxymethyl-1-hydroxy-1-cyclobutyl)methoxy]pyrimidine (compound No. 92)

Step 1; 60% Sodium hydride (0.16 g, 0.04 mol) was suspended in dry dioxane (20 ml) and 3-benzoyloxymethyl-1-hydroxy-1-cyclobutylmethanol (0.95 g, 0.04 mol) dissolved in dry dioxane (10 ml) was dropwise added thereto. The mixture was stirred at 60–70° C. for 30 minutes, and 2-amino-4,6-dichloropyrimidine (0.66 g, 0.04 mol) was added. The mixture was refluxed for 3 hours, and filtrated. The solvent in the filtrate was distilled away under reduced pressure and the residue was purified by silica gel column chromatography (chloroform:methanol=100:1) to give white crystals (0.46 g, 31.5%) of the objective compound No. 91 of 2-amino-6-chloro-4-[(3-benzoyloxymethyl-1-hydroxy-1-cyclobutyl)methoxy]pyrimidine.

Step 2; 2-Amino-6-chloro-4-[(3-benzoyloxymethyl-1-hydroxy-1-cyclobutyl)methoxy]pyrimidine obtained in the same manner as in Step 1 was dissolved in 20 ml of saturated ammonia-methanol solution. The mixture was sealed and allowed to react at room temperature for 4 days. The solvent was distilled away under reduced pressure and the residue was purified by silica gel column chromatography (chloroform:methanol=100:3) to give white crystals (0.28 g, 77.8%) of the objective compound No. 92 of 2-amino-6-chloro-4-[(3-hydroxymethyl-1-hydroxy-1-cyclobutyl)methoxy]pyrimidine, m.p. 128–130° C. (acetone).

METHOD B

PRODUCTION EXAMPLE 9

6-Chloro-2,5-diamino-4-[[(3-phenylmethyloxy-1-hydroxymethyl-1-cyclobutyl)methyl]amino]pyrimidine (compound No. 60)

Step 1; 2-Amino-6-chloro-4-[[(3-phenylmethyloxy-1-hydroxymethyl-1-cyclobutyl)methyl]amino]-5-[(p-chlorophenyl)azo]pyrimidine 2-Amino-6-chloro-4-[[(3-phenylmethyloxy-1-hydroxymethyl-1-cyclobutyl)methyl]amino]pyrimidine (9.15 g, 0.04 mol) was dissolved in a mixture of sodium acetate (48.3 g), acetic acid (200 ml) and water (200 ml), and a cold p-chlorobenzenediazonium chloride solution prepared by dissolving p-chloroaniline (5.61 g, 0.044 mol) in water (40 ml) and conc. hydrochloric acid (12 ml) and dropwise adding thereto sodium nitrite (3.31 g, 0.048 mol) dissolved in water (40 ml) at 2–3° C. was dropwise added at room temperature. The mixture was stirred for one day. The resulting crystals were collected by filtration and washed with water to give orange-yellow crystals (10.07 g, 72.9%), m.p. 142–144° C. (dietheyl ether).

Step 2; 6-Chloro-2,5-diamino-4-[[(3-phenylmethyloxy-1-hydroxymethyl-1-cyclobutyl)methyl]amino]pyrimidine To 2-amino-6-chloro-5-[(p-chlorophenyl)azo]-4-[[(3-phenylmethyloxy- 1-hydroxymethyl-1-cyclobutyl)methyl]amino]pyrimidine (7.34 g, 0.02 mol) were added ethanol (170 ml), water (170 ml), and acetic acid (17 ml), and the mixture was heated to 70° C. A zinc powder (16.5 g) was added portionwise with stirring in a nitrogen stream, and the mixture was stirred at the same temperature for 1.5 hours to give a solution. The reaction mixture was filtered and the solvent in the filtrate was distilled away under reduced pressure. Water was added to the residue and the mixture was extracted with chloroform, washed with water and dried over anhydrous magnesium sulfate. The solvent was distilled away under reduced pressure and the residue was purified by silica gel column chromatography (chloroform:methanol=100:3) to give pale-brown crystals (2.6 g, 53.4%), m.p. 147–149° C. (ethyl acetate).

METHOD C

PRODUCTION EXAMPLE 10, METHOD C-1

2-Amino-5,6-dichloro-4-[[(1-hydroxymethyl-1-cyclobutyl)methyl]amino]pyrimidine (compound No. 33)

To 2-amino-6-chloro-4-[[(1-hydroxymethyl-1-cyclobutyl)methyl]amino]pyrimidine (0.24 g, 2.0 mmol) were added N-chlorosuccinimide (0.27 g, 2.0 mmol) and dimethylformamide (1.5 ml), and the mixture was stirred at room temperature for 2 days. Ethyl acetate was added and the mixture was washed with water and dried over anhydrous magnesium sulfate. The solvent was distilled away under reduced pressure and the residue was purified by silica gel column chromatography (chloroform:methanol=100:1) to give colorless prism crystals (0.3 g, 54.2%), m.p. 179–181° C. (acetone).

PRODUCTION EXAMPLE 11, METHOD C-2

2-Amino-5-bromo-4-[[(1-hydroxymethyl-1-cyclobutyl)methyl]amino]pyrimidine (compound No. 6)

To 2-amino-4-[[(1-hydroxymethyl-1-cyclobutyl)methyl]amino]pyrimidine (0.21 g, 1.0 mmol) was added acetic acid (3 ml) and the mixture was heated to 110° C. Sodium acetate 3 hydrate (0.18 g) was added and bromine (60 μl) dissolved in acetic acid (0.5 ml) was dropwise added at 70° C. After cooling, water was added to the reaction mixture and the mixture was neutralized with aqueous ammonia under ice-cooling, extracted with ethyl acetate and dried over anhydrous magnesium sulfate. The solvent was distilled away under reduced pressure and the residue was recrystallized from acetone to give colorless prism crystals (0.21 g, 72.4%), m.p. 156–158° C. (acetone).

METHOD D

PRODUCTION EXAMPLE 12, METHOD D-1

2-Amino-4-[[(1-hydroxymethyl-1-cyclobutyl)methyl]amino]pyrimidine (compound No. 2)

To 2-amino-6-chloro-4-[[(1-hydroxymethyl-1-cyclobutyl)methyl]amino]pyrimidine (1.46 g, 6.0 mmol) were added ethanol (40 ml), cyclohexene (15 ml) and palladium hydroxide (0.2 g) in a nitrogen stream, and the mixture was refluxed for 2 hours. The reaction mixture was filtered and the solvent in the filtrate was distilled away under reduced pressure to give white amorphous crystals (1.34 g, quantitative).

PRODUCTION EXAMPLE 13, METHOD D-2

2,5-Diamino-4-{[[1-hydroxymethyl-3-(2-phenylethyl)-1-cyclobutyl]methyl]amino}pyrimidine (compound No. 14)

To 2-amino-6-chloro-5-(p-chlorophenyl)azo-4-{[[1-hydroxymethyl-3-(2-phenylethyl)-1-cyclobutyl]methyl]amino}pyrimidine (1.21 g, 2.5 mmol) were added ethanol (40 ml), cyclohexene (15 ml) and palladium hydroxide (0.2 g) in a nitrogen stream, and the mixture was refluxed for one day. The reaction mixture was filtered and the solvent in the filtrate was distilled away under reduced pressure. The residue was purified by silica gel column chromatography (chloroform:methanol=5:1) to give pale-brown crystals (0.43 g, 52.4%), m.p. of hydrochloride 214–217° C. (methanol).

PRODUCTION EXAMPLE 14, METHOD D-3

6-Chloro-2,5-diamino-4-{[[3-(2-phenylethyl)-1-hydroxymethyl-1-cyclobutyl]methyl]amino}pyrimidine (compound No. 64)

To 2-amino-6-chloro-5-(p-chlorophenyl)azo-4-{[[3-(2-phenylethyl)-1-hydroxymethyl-1-cyclobutyl]methyl]amino}pyrimidine (1.21 g, 0.0025 mol) were added ethanol (20 ml), water (20 ml) and acetic acid (2 ml), and the mixture was heated to 70° C. A zinc powder (16.5 g) was added portionwise with stirring in a nitrogen stream, and the mixture was stirred at the same temperature for 2 hours to give a solution. The reaction mixture was filtered and the solvent in the filtrate was distilled away under reduced pressure. Water was added to the residue and the mixture was extracted with chloroform, washed with water and dried over anhydrous magnesium sulfate. The solvent was distilled away under reduced pressure and the residue was purified by silica gel column chromatography (chloroform:methanol=100:1) to give pale-brown crystals (0.74 g, 82.2%), m.p. 149–151° C. (ethyl acetate).

METHOD E

PRODUCTION EXAMPLE 15

2-Amino-6-chloro-4-[[(1-hydroxymethyl-3-oxo-1-cyclobutyl)methyl]-amino]pyrimidine (compound No. 41)

To 2-amino-6-chloro-4-[[(1-hydroxymethyl-3,3-dimethoxy-1-cyclobutyl)methyl]amino]pyrimidine (0.61 g, 2.0 mmol) were added acetone (50 ml) and 20% hydrochloric acid (0.5 ml), and the mixture was refluxed for 30 minutes. The mixture was neutralized with 10% ammonia-methanol under ice-cooling. The solvent was distilled away under reduced pressure and the residue was recrystallized from acetone to give colorless prism crystals (0.36 g, 70.1%), m.p. 171–173° C. (acetone).

METHOD F

PRODUCTION EXAMPLE 16

2-Amino-6-chloro-4-[[(1-hydroxymethyl-3-hydroxy-1-cyclobutyl)methyl]-amino]pyrimidine (compound No. 38)

2-Amino-6-chloro-4-[[(1-hydroxymethyl-3-oxo-1-cyclobutyl)methyl]-amino]pyrimidine (2.21 g, 8.26 mmol) was dissolved in ethanol (80 ml) and sodium borohydride (0.31 g, 8.26 mmol) was added portionwise under ice-cooling. The mixture was stirred at room temperature for 30 minutes. The mixture was neutralized with hydrochloric acid-ethanol. The solvent was distilled away under reduced pressure and the residue was purified by silica gel column chromatography (chloroform:methanol=100:7) to give white crystals (2.14 g, quantitative), m.p. 136–139° C. (ethyl acetate).

METHOD G

PRODUCTION EXAMPLE 17

2-Amino-6-chloro-4-[[(3-hydroxy-3-hydroxymethyl-1-cyclobutyl)methyl]-amino]pyrimidine (compound No. 27)

2-Amino-6-chloro-4-[[(3-methylene-1-cyclobutyl)methyl]amino]-pyrimidine (1.12 g, 0.005 mol) was dissolved in acetone (15 ml) and water (10 ml), and N-methylmorpholine N-oxide (0.64 g, 0.0055 mol) and osmium tetraoxide (3 mg) were added. The mixture was stirred for 5 hours in a nitrogen stream, and the solvent was distilled away under reduced pressure. The residue was purified by silica gel column chromatography (chloroform:methanol=100:7, later 10:1) to give colorless prism crystals (0.96 g, 74.4%), m.p. 158–160° C. (ethanol).

METHOD H

PRODUCTION EXAMPLE 18

2-Amino-6-chloro-5-hydroxymethyl-4-[[(1-hydroxymethyl-1-cyclobutyl)-methyl]amino]pyrimidine (compound No. 72)

2-Amino-6-chloro-4-[[(1-hydroxymethyl-1-cyclobutyl) methyl]amino]-5-formylpyrimidine (0.54 g, 2.0 mmol) was dissolved in ethanol (20 ml) and sodium borohydride (40 mg, 1.0 mmol) was added. The mixture was stirred at room temperature for 30 minutes. Then, acetic acid (0.1 ml) was added and the solvent was distilled away under reduced pressure. The residue was extracted with hot acetone to give colorless prism crystals (0.45 g, 81.8%), m.p. 160–162° C. (acetone).

METHOD I

PRODUCTION EXAMPLE 19

2-Amino-6-chloro-4-{[[1-hydroxymethyl-3-(2-phenylethyl)-1-cyclobutyl]methyl]amino}-5-carbaldehydeoximepyrimidine (compound No. 79)

To 2-amino-6-chloro-4-{[[1-hydroxymethyl-3-(2-phenylethyl)-1-cyclobutyl]methyl]amino}-5-formylpyrimidine (0.75 g, 2.0 mmol) were added hydroxylamine hydrochloride (0.14 g, 2.2 mmol) and ethanol (30 ml), and the mixture was refluxed for 2 hours. The mixture was neutralized with an ammonia-methanol solution under ice-cooling. The solvent was distilled away under reduced pressure and the residue was extracted with hot acetone. The solvent was distilled away under reduced pressure to give pale-yellow crystals (0.75 g, 96.2%), m.p. 154–156° C. (ether).

METHOD J

PRODUCTION EXAMPLE 20

2-Amino-4-{[[1-hydroxymethyl-3-(2-phenylethyl)-1-cyclobutyl]methyl]-amino}-5-cyanopyrimidine (compound No. 11)

Step 1; 2-Amino-4-[1-acetoxymethyl-3-(2-phenylethyl)-1-cyclobutylmethylamino]-5-cyanopyrimidine (compound No. 12)

Acetic acid (25 ml) was added to 2-amino-4-[1-hydroxymethyl-3-(2-phenylethyl)-1-cyclobutylmethylamino]-5-carbaldehydeoximepyrimidine hydrochloride (1.18 g, 3.0 mmol) and the mixture was refluxed for 16 hours. The solvent was distilled away under reduced pressure and the residue was purified by silica gel column chromatography (chloroform:methanol=100:1) to give pale-yellow prism crystals (0.26 g, 22.8%), m.p. 156–159° C. (methanol).

Step 2; 2-Amino-4-[1-hydroxymethyl-3-(2-phenylethyl)-1-cyclobutylmethylamino]-5-cyanopyrimidine (compound No. 11)

A saturated ammonia-methanol solution (50 ml) was added to 2-amino-4-[1-acetoxymethyl-3-(2-phenylethyl)-1-cyclobutylmethylamino]-5-cyanopyrimidine (0.95 g, 2.5 mmol), and the mixture was allowed to stand at room temperature for one day. The solvent was distilled away under reduced pressure and the residue was purified by silica gel column chromatography (chloroform:methanol=50:1) to give pale-yellow prism crystals (0.61 g, 71.4%), m.p. 184–189° C. (methanol).

The compounds of the foregoing Examples and Production Examples, and the compounds of the formula [I'] produced in the same manner as the above-mentioned Production Examples are shown in the following Tables. It is needless to say that the present invention is not limited to these compounds.

In the following Tables, abbreviations stand for the following.

MeOH: methanol

EtOH: ethanol

Et2O: ethyl ether iso-PrOH: isopropanol

AcOEt: ethyl acetate dec: decomposition

Those without $^1$H NMR determination solvent in the Tables were determined in DMSO-$d_6$.

TABLE 1

[I]

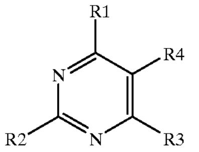

| compound No. | R1 | R2 | R3 | R4 | m.p. (° C.) recrystallization solvent | $^1$H-NMR (60 MHz) | mass spectrum EIm/z CIm/z |
|---|---|---|---|---|---|---|---|
| 1 | H | —NH2 | 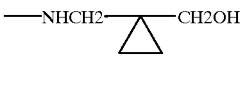 | H | 110–115 | 0.52(br, 4H), 3.4(s, 2H), 3.45 (d, 2H), 4.1(br, 1H), 6.3(d, 1H) 7.52(d, 1H), 7.56(br, 2H), 8.85(t, 1H) | 194 195 |
| 2 | H | —NH2 | 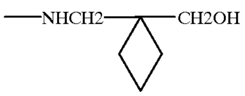 | H | — | 1.85(s, 6H), 3.5(s, 2H), 3.6(d, 2H) 4.25(br, 1H), 6.33(d, 1H), 7.58(d, 1H), 7.7(br, 2H), 8.9(t, 1H) | 208 209 |

TABLE 1-continued

[I]

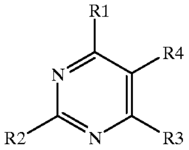

| compound No. | R1 | R2 | R3 | R4 | m.p. (° C.) recrystallization solvent | $^1$H-NMR (60 MHz) | mass spectrum EIm/z CIm/z |
|---|---|---|---|---|---|---|---|
| 3 | H | —NH2 | 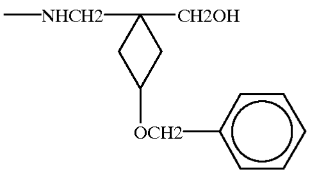 | H | 161–163 acetone | 1.5–2.4(m, 4H), 3.3(s, 2H), 3.35 (d, 2H), 3.8–4.3(m, 1H), 4.35(s, 2H), 4.9(br, 1H), 5.65(br, 2H), 5.75(d, 1H), 7.6(d, 1H), 6.7(t, 1H), 7.27(s, 5H) | 314 315 |
| 4 | H | —NH2 | 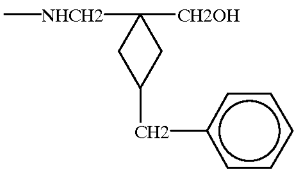 | H | — | 1.4–2.1(m, 5H), 2.65(br, 2H), 3.4(br, 4H), 4.18(br, 1H), 6.28(d, 1H), 7.15(s, 5H), 7.55 (d, 1H), 7.7(br, 2H), 8.78(t, 1H) | 298 299 |
| 5 | H | —NH2 | 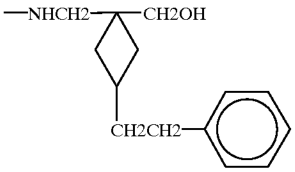 | H | — | 1.2–2.2(m, 7H), 2.5(t, 2H), 3.5(br, 4H), 4.5(br, 1H), 6.3(d, 1H), 7.2(s, 1H), 7.56(d, 1H), 8.8(br, 1H) | 312 313 |

TABLE 2

| compound No. | R1 | R2 | R3 | R4 | m.p. (° C.) recrystallization solvent | $^1$H-NMR (60 MHz) | mass spectrum EIm/z CIm/z |
|---|---|---|---|---|---|---|---|
| 6 | H | —NH2 | 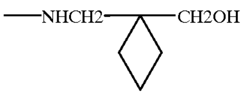 | Br | 156–158 acetone | 1.8(b, 6H), 3.45(d, 2H), 3.5 (d, 2H), 4.85(t, 1H), 6.0(br, 2H), 6.45(t, 1H), 7.73(s, 1H) | 286 287 |
| 7 | H | —NH2 | 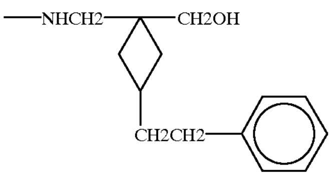 | Br | 156–160 acetone | 1.2–2.2(m, 7H), 2.5(t, 2H), 3.45(d, 2H), 3.5(br, 2H), 4.8(br, 1H), 5.9(br, 2H), 6.45(t, 1H), 7.19 (s, 5H), 7.76(s, 1H) | 390, 392 391, 393 |
| 8 | H | —NH2 | 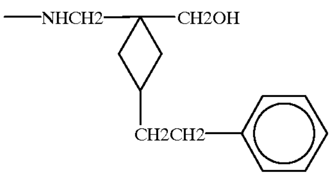 | Cl | 157–159 acetone | 1.2–2.1(m, 7H), 2.53(t, 2H), 3.48(d, 4H), 4.1(br, 1H), 5.34 (br, 2H), 6.16(t, 1H), 7.15(s, 5H), 7.66(s, 1H) | 346 347 |

TABLE 2-continued

| compound No. | R1 | R2 | R3 | R4 | m.p. (° C.) recrystallization solvent | $^1$H-NMR (60 MHz) | mass spectrum EIm/z CIm/z |
|---|---|---|---|---|---|---|---|
| 9 | H | —NH2 | 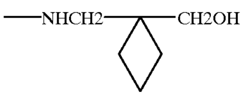 | I | 146–148 acetone | 1.83(br, 6H), 3.48(S, 2H), 3.53 (d, 2H), 5.0(br, 2H), 5.6(t, 1H), 7.92(s, 1H) | 334 335 |
| 10 | H | —NH2 | 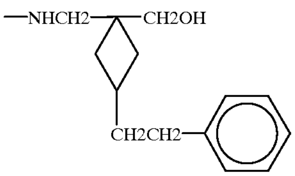 | I | 151–153 acetone | 1.3–2.2(m, 7H), 2.54(t, 2H), 3.45–3.65(m, 4H), 5.6(br, 3H), 6.5(t, 1H), 7.15(s, 5H), 7.91(s, 1H) | 438 438 |

TABLE 3

| compound No. | 1 | R2 | R3 | R4 | m.p. (° C.) recrystallization solvent | $^1$H-NMR (60 MHz) | mass spectrum EIm/z CIm/z |
|---|---|---|---|---|---|---|---|
| 11 | H | —NH2 | 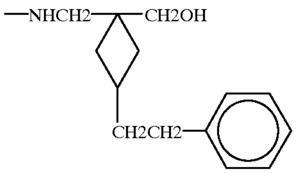 | —CN | 184–189 MeOH | 1.3–2.2(m, 7H), 2.52(t, 2H), 3.47(d, 4H), 4.83(t, 1H), 6.82 (br, 2H), 7.18(s, 5H), 8.06(s, 1H) | 337 338 |
| 12 | H | —NH2 | 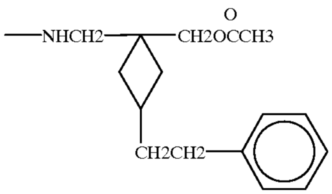 | —CN | 156–159 MeOH | 1.3–2.2(m, 7H), 2.1(s, 3H), 2.5(t, 2H), 3.5(d, 2H), 4.13 (s, 2H), 5.48(br, 2H), 5.78(t, 1H), 7.12(s, 5H), 8.0(s, 1H) | 379 380 |
| 13 | H | —NH2 | 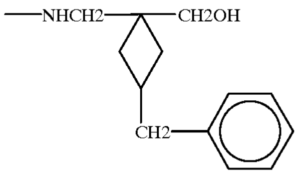 | —NH2 | — | 1.4–2.2(m, 5H), 2.7(br, 2H), 3.57(d, 2H), 3.73(d, 2H), 4.77 (br, 6H), 7.2(s, 5H), 7.3(s, 1H) | 313 314 |
| 14 | H | —NH2 | 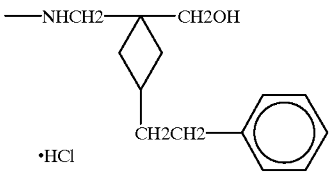 •HCl | —NH2 | 214–217 MeOH | 1.3–2.2(m, 7H), 2.55(t, 2H), 3.55(d, 2H), 3.7(d, 2H), 4.75 (s, 6H), 7.17(s, 5H), 7.21(s, 1H) | 327 328 |
| 15 | H | —NH2 | 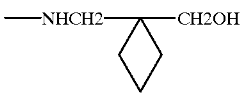 | —CH═NOH | 201–206 acetone | 1.8(br, 6H), 3.4(s, 2H), 3.6 (d, 2H), 4.1(br, 2H), 6.22(br, 2H), 7.76(s, 1H), 7.95(s, 1H), 8.07(t, 1H) | 251 252 |

TABLE 4

| compound No. | R1 | R2 | R3 | R4 | m.p. (° C.) recrystallization solvent | $^1$H-NMR (60 MHz) | mass spectrum EIm/z CIm/z |
|---|---|---|---|---|---|---|---|
| 16 | H | —NH2 | 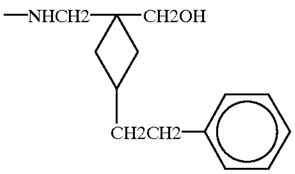 | —CH=NOH | 170–176 acetone | 1.2–2.2(m, 7H), 2.5(t, 2H), 3.45 (br, 2H), 3.53(d, 2H), 4.0–5.4 (br, 2H), 6.33(br, 2H), 7.2(s, 5H), 7.82(s, 1H), 8.0(s, 1H), 8.14(t, 1H) | 355 356 |
| 17 | Cl | H | 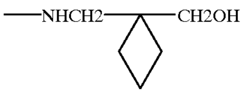 | H | 117–118 CHC13 | 1.65(s, 6H), 3.25(s, 4H), 4.5(s, 2H), 6.3(s, 1H), 7.95(s, 1H) (CD3OD) | 227 228 |
| 18 | Cl | H | 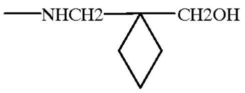 | —NH2 | 137–138 AcOEt | 1.65(s, 6H), 3.25(s, 2H), 3.4(s, 2H), 4.5(s, 4H), 7.50(s, 1H) (CD3OD) | 242 243 |
| 19 | Cl | —NH2 | 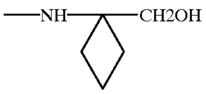 | H | 233–235 MeOH | 1.6–2.4(m, 6H), 3.65(d, 2H), 4.85(t, 1H), 5.7(s, 1H), 6.05 (br, 2H), 7.0(br, 1H) | 228 229 |
| 20 | Cl | —NH2 | 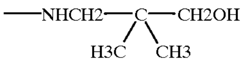 | H | 203–207 CHC13—MeOH | 0.83(s, 6H), 3.08(s, 2H), 3.1 (d, 2H), 4.5(br, 1H), 5.79(s, 1H), 6.13(s, 2H), 6.90(t, 1H) | 230 231 |

TABLE 5

| compound No. | R1 | R2 | R3 | R4 | m.p. (° C.) recrystallization solvent | $^1$H-NMR (60 MHz) | mass spectrum EIm/z CIm/z |
|---|---|---|---|---|---|---|---|
| 21 | Cl | —NH2 | 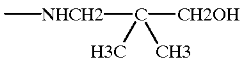 | —CHO | 177–179 acetone | 0.9(s, 6H), 3.18(d, 2H), 3.38(d, 2H), 4.45(t, 1H), 7.15(br, 2H), 9.4(t, 1H), 9.98(s, 1H) | 258 259 |
| 22 | Cl | —NH2 | 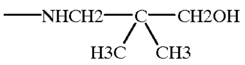 | —CH=NOH | 205–209 acetone | 0.9(s, 6H), 3.15(d, 2H), 3.35(d, 2H), 4.45(t, 1H), 6.4(br, 2H), 8.33(s, 1H), 8.53(t, 1H), 10.88 (s, 1H) | 273 274 |
| 23 | Cl | —NH2 | 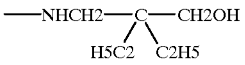 | H | 185–187 CHC13 | 0.8(t, 6H), 1.10(q, 4H), 3.1(d, 4H), 4.60(t, 1H), 5.80(s, 1H), 6.30(s, 2H), 6.80(t, 1H) | 258 259 |
| 24 | Cl | —NH2 | 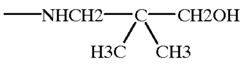 | —NH2 | 223–228 MeOH | 0.9(s, 6H), 3.18(s, 2H), 3.29(s, 2H), 4.38(br, 6H) (CD3OD) | 245 246 |
| 25 | Cl | —NH2 | 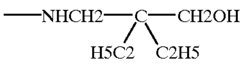 | —NH2 | 185–197 MeOH | 0.85(t, 6H), 1.25(q, 4H), 3.2(s, 2H), 3.3(s, 2H), 4.27(s, 6H) (CD3OD) | 273 274 |

TABLE 6

| compound No. | R1 | R2 | R3 | R4 | m.p. (° C.) recrystallization solvent | $^1$H-NMR (60 MHz) | mass spectrum EIm/z CIm/z |
|---|---|---|---|---|---|---|---|
| 26 | Cl | —NH2 | 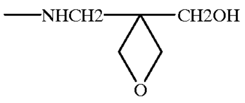 | H | 185–186 acetone | 3.6(d, 4H), 4.35(s, 4H), 4.83(t, 1H), 5.8(s, 1H), 6.18(br, 2H), 7.07(t, 1H) | 244 245 |
| 27 | Cl | —NH2 | 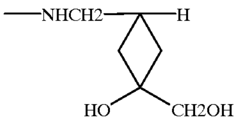 | H | 158–160 EtOH | 1.6–2.4(m, 5H), 3.35(br, 2H), 4.28(t, 1H), 4.53, 4.6(each s, 1H), 5.75(s, 1H), 5.87(br, 2H), 6.73(t, 1H) | 258 259 |
| 28 | Cl | —NH2 | 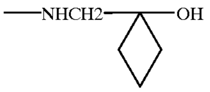 | H | 205–207 acetone | 1.2–2.2(m, 6H), 3.42(d, 2H), 5.2(s, 1H), 5.87(s, 1H), 6.0(br, 2H), 6.7(br, 1H) | 228 229 |
| 29 | Cl | —NH2 | 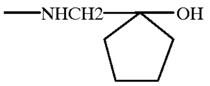 | H | 194–196 MeOH | 1.6(br, 8H), 3.35(d, 2H), 4.5(s, 1H), 5.9(s, 1H), 6.2(br, 2H), 6.88(t, 1H) | 242 243 |
| 30 | Cl | —NH2 | 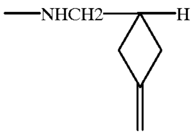 | H | 82–84 Et20-hexane | 2.2–2.9(m, 5H), 3.36(br, 2H), 4.78(br, 2H), 5.8(s, 1H), 5.91 (br, 2H), 6.88(t, 1H) | 224 225 |

TABLE 7

| compound No. | R1 | R2 | R3 | R4 | m.p. (° C.) recrystallization solvent | $^1$H-NMR (60 MHz) | mass spectrum EIm/z CIm/z |
|---|---|---|---|---|---|---|---|
| 31 | Cl | —NH2 | 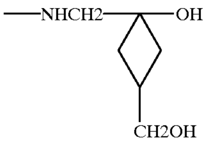 | H | 60–70 | 1.5–2.4(m, 5H), 3.33(d, 2H), 3.5 (d, 2H), 4.35(t, 1H), 5.06, 5.17 (each s, 1H), 5.85, 5.88(each s, 1H), 6.0(br, 2H), 6.7(br, 1H) | 258 259 |
| 32 | Cl | —NH2 | 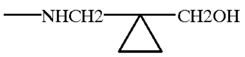 | H | 171–173 acetone | 0.42(br, 4H), 3.25(d, 2H), 3.3 (d, 2H), 4.52(t, 1H), 5.8(s, 1H), 5.97(br, 2H), 6.85(t, 1H) | 228 229 |
| 33 | Cl | —NH2 | 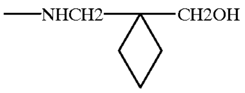 | Cl | 179–181 acetone | 1.86(br, 6H), 3.55(d, 4H), 4.66 (t, 1H), 5.68(s, 2H), 6.63(t, 1H) | 276, 278 277, 279 |
| 34 | Cl | —NH2 | 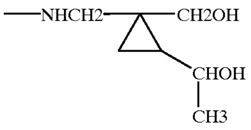 | H | 169–171 acetone | 0.2–1.0(m, 3H), 1.25(d, 3H), 2.7–4.0(m, 5H), 4.47(d, 1H), 4.85(t, 1H), 5.81(s, 1H), 5.96 (br, 2H), 6.83(t, 1H) | 272 273 |
| 35 | Cl | —NH2 | 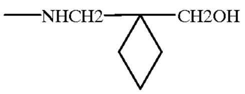 | H | 192–194 acetone | 1.78(br, 6H), 3.38(d, 4H), 4.63 (t, 1H), 5.8(s, 1H), 6.1(br, 2H), 6.87(t, 1H) | 242 243 |

TABLE 8

| compound No. | R1 | R2 | R3 | R4 | m.p. (° C.) recrystal-lization solvent | $^1$H-NMR (60 MHz) | mass spectrum EIm/z CIm/z |
|---|---|---|---|---|---|---|---|
| 36 | Cl | —NH2 | 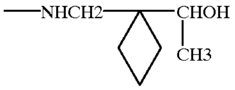 | H | 149–150 AcOEt | 1.2(d, 3H), 1.98(br, 6H), 3.45 (d, 2H), 3.6–4.0(m, 1H), 4.4–4.9 (br, 1H), 5.5(s, 2H), 5.78(s, 1H), 6.52(t, 1H) | 255 256 |
| 37 | Cl | —NH2 | 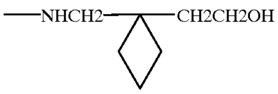 | H | 105–107 Et2O | 1.85(br, 8H), 3.48(d, 2H), 3.7 (t, 2H), 5.23(br, 2H), 5.6(t, 1H), 5.75(s, 1H) | 257 257 |
| 38 | Cl | —NH2 | 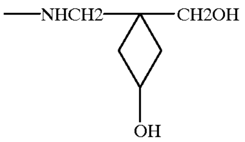 | H | 136–139 AcOEt | 1.4–2.3(m, 4H), 3.35(d, 4H), 3.8–4.4(m, 1H), 4.7(br, 1H), 4.77(t, 1H), 5.83(s, 1H), 6.1 (br, 2H), 6.95(t, 1H) | 258 259 |
| 39 | Cl | —NH2 | 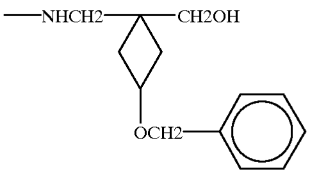 | H | 137–138 Et20 | 1.5–2.4(m, 4H), 3.4(br, 4H), 3.85–4.3(m, 1H), 4.35(s, 2H), 4.75(br, 1H), 5.55(br, 2H), 5.78 (s, 1H), 6.7(t, 1H), 7.27 s, 5H) | 348 349 |
| 40 | Cl | —NH2 | 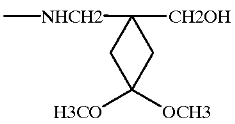 | H | 159–162 acetone | 1.85(s, 4H), 3.02(s, 6H), 3.3 (d, 4H), 4.6(t, 1H), 5.7(s, 1H), 6.15(br, 2H), 6.9(t, 1H) | 302 303 |

TABLE 9

| compound No. | R1 | R2 | R3 | R4 | m.p. (° C.) recrystal-lization solvent | $^1$H-NMR (60 MHz) | mass spectrum EIm/z CIm/z |
|---|---|---|---|---|---|---|---|
| 41 | Cl | —NH2 | 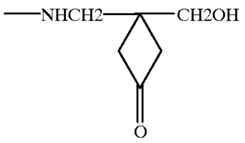 | H | 171–173 acetone | 2.8(s, 4H), 3.45(d, 2H), 3.47(d, 2H), 4.85(t, 1H), 5.7(s, 1H), 6.23 (s, 2H), 7.1(t, 1H) | 256 257 |
| 42 | Cl | —NH2 | 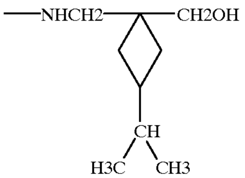 | H | 183–185 acetone | 0.75(d, 6H), 1.1–2.0(m, 6H), 3.1–3.55(m, 4H), 4.6(t, 1H), 5.79, 5.81(each s, 1H), 5.92 (br, 2H), 6.78(br, 1H) | 284 285 |

TABLE 9-continued

| compound No. | R1 | R2 | R3 | R4 | m.p. (° C.) recrystallization solvent | $^1$H-NMR (60 MHz) | mass spectrum EIm/z CIm/z |
|---|---|---|---|---|---|---|---|
| 43 | Cl | —NH2 | 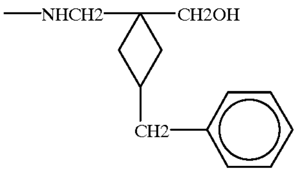 | H | 161–163 AcoEt | 1.3–2.1(m, 5H), 2.67(br, 2H), 3.4(br, 4H), 4.7(br, 1H), 5.83 (s, 1H), 6.0(br, 2H), 6.9(br, 1H), 7.2(s, 5H) | 332 333 |
| 44 | Cl | —NH2 | 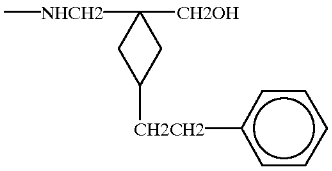 | H | 167–169 acetone | 1.2–2.2(m, 7H), 2.5(t, 2H), 3.3 (d, 4H), 3.43(br, 2H), 4.7 (br, 1H), 5.5(s, 2H), 5.73(s, 1H), 6.5(t, 1H), 7.07(s, 5H) | 346 347 |
| 45 | Cl | —NH2 | 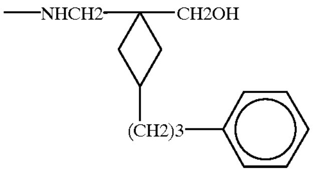 | H | 154–156 acetone | 1.2–2.1(m, 9H), 2.57(br, 2H), 3.3(br, 4H), 4.15(br, 1H), 5.8(s, 1H), 6.17(br, 2H), 6.9 (br, 1H), 7.2(s, 5H) | 360 361 |

TABLE 10

| compound No. | R1 | R2 | R3 | R4 | m.p. (° C.) recrystallization solvent | $^1$H-NMR (60 MHz) | mass spectrum EIm/z CIm/z |
|---|---|---|---|---|---|---|---|
| 46 | Cl | —NH2 | 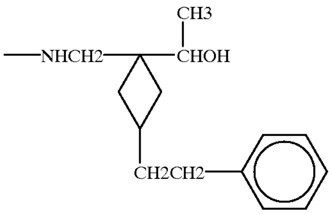 | H | 125–132 AcOEt | 1.2(d, 3H), 1.3–2.3(m 7H), 2.5(t, 2H), 3.15–3.55(m, 2H), 3.6–4.0 (m, 1H), 4.2–4.6(br, 1H), 5.3(s, 2H), 5.75(s, 1H), 6.3(t, 1H), 7.15(s, 5H) | 360 361 |
| 47 | Cl | —NH2 | 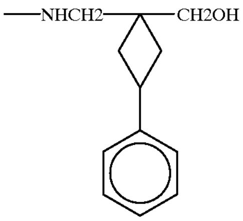 | H | 180–183 acetone | 1.7–2.5(m, 5H), 3.4(br, 2H), 3.62 (br, 2H), 4.25(br, 1H), 5.83, 5.88(each s, 1H), 6.15(br, 2H), 7.1(br, 1H), 7.28(s, 5H) | 318 319 |
| 48 | Cl | —NH2 | 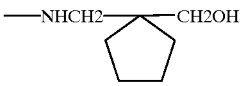 | H | 196–198 acetone | 1.5(br, 8H), 3.25(d, 4H), 4.85 (t, 1H), 5.82(s, 1H), 6.07(br, 2H), 6.97(t, 1H) | 256 257 |

TABLE 10-continued

| compound No. | R1 | R2 | R3 | R4 | m.p. (° C.) recrystallization solvent | $^1$H-NMR (60 MHz) | mass spectrum EIm/z CIm/z |
|---|---|---|---|---|---|---|---|
| 49 | Cl | —NH2 | 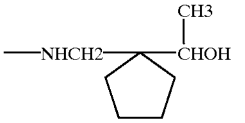 | H | 155–157 AcOEt | 1.15(d, 3H), 1.6(br, 8H), 2.9–3.9 (m, 3H), 5.0(br, 1H), 5.78(s, 3H), 6.85(t, 1H) | 270 271 |
| 50 | Cl | —NH2 | 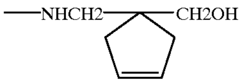 | H | 201–203 acetone | 2.1(s, 4H), 3.1–3.5(m, 4H), 4.75 (t, 1H), 5.55(s, 2H), 5.8(s, 1H), 6.35(br, 2H), 7.0(br, 1H) | 254 255 |

TABLE 11

| compound No. | R1 | R2 | R3 | R4 | m.p. (° C.) recrystallization solvent | $^1$H-NMR (60 MHz) | mass spectrum EIm/z CIm/z |
|---|---|---|---|---|---|---|---|
| 51 | Cl | —NH2 | 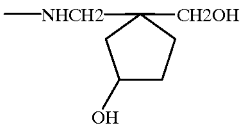 | H | 188–190 acetone | 1.4–1.8(m, 6H), 3.18(d, 2H), 3.28 (d, 2H), 4.0–4.4(m, 1H), 4.5(d, 1H), 4.77(t, 1H), 5.76(s, 1H), 6.1(br, 2H), 7.05(t, 1H) | 272 273 |
| 52 | Cl | —NH2 | 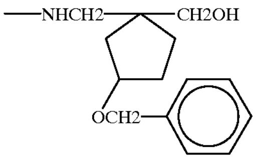 | H | 115–118 Et20 | 1.5–2.0(m, 6H), 3.2–3.6(m, 4H), 3.9–4.3(m, 1H), 4.47(s, 2H), 5.05(br, 2H), 5.5(t, 1H), 5.52 (s, 1H), 7.32(s, 5H) (CDCl3) | 362 363 |
| 53 | Cl | —NH2 | 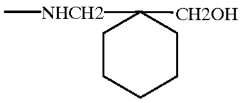 | H | 221–222 acetone | 1.28(br, 10H), 3.1–3.5(m, 4H), 4.52(t, 1H), 5.78(s, 1H), 6.27(br, 2H), 6.85(t, 1H) | 270 271 |
| 54 | Cl | —NH2 | 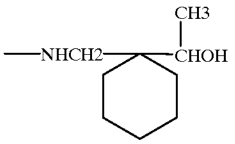 | H | 180–182 acetone | 1.05(d, 3H), 1.43(br, 10H), 3.0–3.7(m, 3H), 3.82(br, 1H), 5.68(s, 2H), 5.73(s, 1H), 6.72(t, 1H) | 284 285 |
| 55 | Cl | —NH2 | 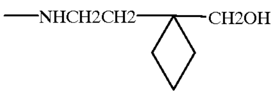 | H | oily substance | 1.75(br, 8H), 3.0–3.5(m, 2H), 3.4(br, 2H), 4.4(br, 1H), 5.74(s, 1H), 6.05(br, 2H), 6.75(t, 1H) | 256 257 |

TABLE 12

| compound No. | R1 | R2 | R3 | R4 | m.p. (° C.) recrystal-lization solvent | $^1$H-NMR (60 MHz) | mass spectrum EIm/z CIm/z |
|---|---|---|---|---|---|---|---|
| 56 | Cl | —NH2 | 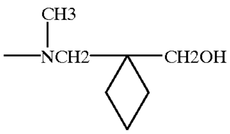 | H | 167–171 acetone | 1.76(br, 6H), 2.95(s, 3H), 3.3 (d, 2H), 3.5(s, 2H), 4.6(t, 1H), 5.85(s, 1H), 6.32(br, 2H) | 256 257 |
| 57 | Cl | —NH2 | 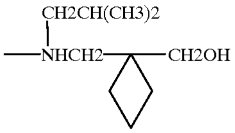 | H | 133–135 acetone | 0.94(d, 6H), 1.87(br, 6H), 1.7–2.4 (m, 1H), 3.13(d, 2H), 3.44(d, 2H), 3.68(s, 2H), 5.02(t, 1H), 5.30(br, 2H), 5.9(s, 1H) (CDCl3) | 298 299 |
| 58 | Cl | —NH2 | 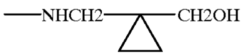 | —NH2 | 172–174 acetone | 0.45(br, 4H), 3.3(s, 2H), 3.35 (d, 2H), 4.0–5.0(br, 5H), 6.5 (t, 1H) | 243 244 |
| 59 | Cl | —NH2 | 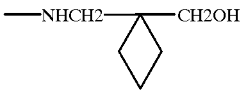 | —NH2 | 226–229 acetone | 1.8(br, 6H), 3.38(s, 2H), 3.5(d, 2H), 3.0–5.0(br, 3H), 5.5 (br, 2H), 6.45(t, 1H) | 257 258 |
| 60 | Cl | —NH2 | 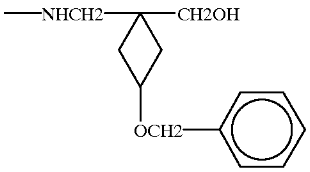 | —NH2 | 147–149 AcOEt | 1.6–2.4(m, 4H), 3.4(br, 4H), 3.54 (d, 2H)3.8–4.3(m, 1H), 4.38(s, 2H) 3.0–5.0(br, 3H), 5.1(br, 2H), 6.55(t, 1H), 7.32(s, 5H) | 363 364 |

TABLE 13

| compound No. | R1 | R2 | R3 | R4 | m.p. (° C.) recrystal-lization solvent | $^1$H-NMR (60 MHz) | mass spectrum EIm/z CIm/z |
|---|---|---|---|---|---|---|---|
| 61 | Cl | —NH2 | 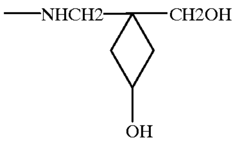 | —NH2 | — | 1.5–2.5(m, 4H), 3.47(s, 2H), 3.55(s, 2H), 4.0–4.5(m, 1H), 4.72(s, 7H) ($CD_3OD$) | 273 274 |
| 62 | Cl | —NH2 | 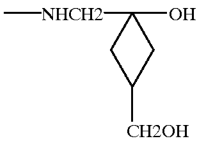 | —NH2 | oily substance | 1.5–2.5(m, 5H), 3.5(s, 2H), 3.55 (s, 2H), 4.75(s, 7H) | 273 274 |
| 63 | Cl | —NH2 | 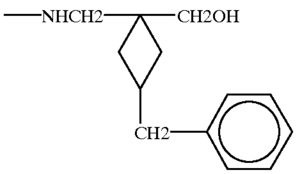 | —NH2 | 100–115 | 1.3–2.1(m, 5H), 2.68(br, 2H), 3.35(d, 2H), 3.45(d, 2H), 4.5(s, 6H), 7.23(s, 5H)($CD_3OD$) | 347 348 |

TABLE 13-continued

| compound No. | R1 | R2 | R3 | R4 | m.p. (° C.) recrystallization solvent | $^1$H-NMR (60 MHz) | mass spectrum EIm/z CIm/z |
|---|---|---|---|---|---|---|---|
| 64 | Cl | —NH2 | 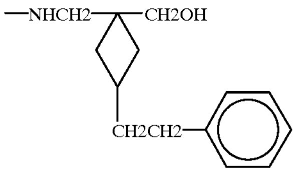 | —NH2 | 149–151 | 1.2–2.1(m, 7H), 2.52(t, 2H), 3.38(d, 2H), 3.48(d, 2H), 4.31 (s, 6H), 7.18(s, 5H) | 361<br>362 |
| 65 | Cl | —NH2 | 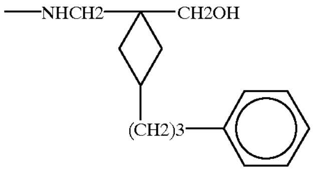 | —NH2 | — | 1.3–2.2(m. 9H), 2.6(br, 2H), 3.2–3.8(m, 4H), 4.9(s, 6H), 7.23(s, 5H) ($CD_3OD$) | 375<br>376 |

TABLE 14

| compound No. | R1 | R2 | R3 | R4 | m.p. (° C.) recrystallization solvent | $^1$H-NMR (60 MHz) | mass spectrum EIm/z CIm/z |
|---|---|---|---|---|---|---|---|
| 66 | Cl | —NH2 | 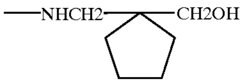 | —NH2 | 225–227 | 1.53(br, 8H), 3.2(s, 2H), 3.35 (d, 2H), 3.0–4.5(br, 3H), 5.45 (br, 2H), 6.55(t, 1H) | 271<br>272 |
| 67 | Cl | —NH2 | 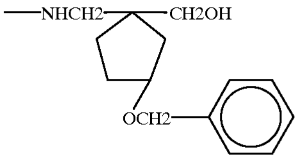 | —NH2 | 125–127<br>AcOEt | 1.5–2.0(m, 6H), 3.3–3.5(m, 4H), 3.9–4.3(m, 1H), 4.5(s, 2H), 4.63 (s, 6H), 7.37(s, 5H) ($CD_3OD$) | 377<br>378 |
| 68 | Cl | —NH2 | 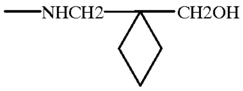 | —CHO | 159–161<br>AcOEt | 1.85(br, 6H), 3.45(d, 2H), 3.6 (d, 2H), 4.28(t, 1H), 6.63(s, 2H), 9.42(t, 1H), 10.01(s, 1H) | 270<br>271 |
| 69 | Cl | —NH2 | 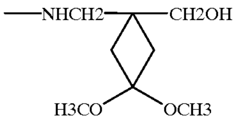 | —CHO | 166–168<br>acetone | 1.9(s, 4H), 3.05(s, 6H), 3.43 (d, 2H), 3.62(d, 2H), 4.68 (t, 1H), 7.37(br, 2H), 9.33(t, 1H), 9.92(s, 1H) | 298(—OCH3)<br>331 |
| 70 | Cl | —NH2 | 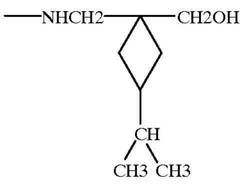 | —CHO | 156–158<br>acetone | 0.8(d, 6H), 1.2–2.1(m, 6H), 3.2–3.8(m, 4H), 4.55(m, 1H), 7.38 (br, 2H), 9.35(br, 1H), 9.95 (s, 1H) | 312<br>313 |

TABLE 15

| compound No. | R1 | R2 | R3 | R4 | m.p. (° C.) recrystal-lization solvent | $^1$H-NMR (60 MHz) | mass spectrum EIm/z CIm/z |
|---|---|---|---|---|---|---|---|
| 71 | Cl | —NH2 | 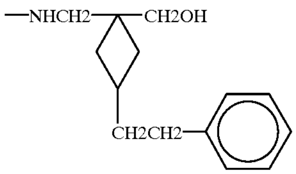 | —CHO | 130–137 Et20 | 1.1–2.2(m, 7H), 2.53(t, 2H), 3.3–3.75(m, 4H), 4.13(t, 1H), 5.97 (s, 2H), 7.18(s, 5H), 9.45(t, 1H), 10.05(s, 1H) | 374 375 |
| 72 | Cl | —NH2 | 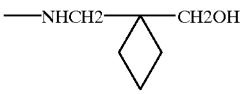 | —CH2OH | 160–162 acetone | 1.80(br, 6H), 3.4(d, 2H), 3.5(d, 2H), 4.48(d, 2H), 4.6–5.0(m, 2H), 5.85(br, 2H), 6.65(t, 1H) | 272 273 |
| 73 | Cl | —NH2 | 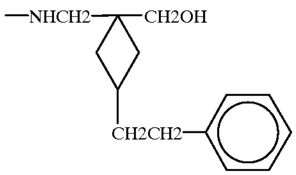 | —CH2OH | 167–170 acetone | 1.1–2.2(m, 7H), 2.48(t, 2H), 3.44(d, 4H), 4.5(d, 2H), 4.6–4.95(m, 2H), 5.65(s, 2H), 6.63 (t, 1H), 7.15(s, 5H) | 376 377 |
| 74 | Cl | —NH2 | 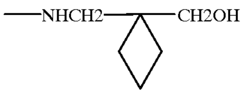 | —CH═NOH | 205–206 AcOEt | 1.80(br, 6H), 3.38(d, 2H), 3.67 (d, 2H), 4.43(t, 1H), 6.38(s, 2H), 8.33(s, 1H), 8.54(t, 1H), 10.85(s, 1H) | 285 286 |
| 75 | Cl | —NH2 | 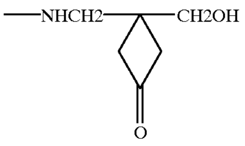 | —CH═NOH | >200 (dec) acetone-H2O | 2.86(s, 4H), 3.6(br, 2H), 3.8(d, 2H), 5.0(br, 1H), 6.75(br, 2H), 8.33(s, 1H), 8.6(t, 1H), 11.05 (s, 1H) | 299 300 |

TABLE 16

| compound No. | R1 | R2 | R3 | R4 | m.p. (° C.) recrystal-lization solvent | $^1$H-NMR (60 MHz) | mass spectrum EIm/z CIm/z |
|---|---|---|---|---|---|---|---|
| 76 | Cl | —NH2 | 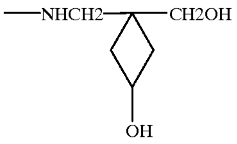 | —CH═NOH | >210 (dec) acetone | 1.4–2.4(m, 4H), 3.4(br, 2H), 3.57 (d, 2H), 3.9–4.3(m, 1H), 4.52(t, 1H), 4.8(d, 1H), 6.52(br, 2H), 8.35 (s, 1H), 8.5(br, 1H), 10.9(s, 1H) | 301 302 |
| 77 | Cl | —NH2 | 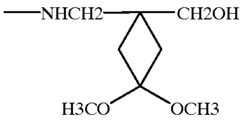 | —CH═NOH | >200 (dec) acetone | 1.9(s, 4H), 3.06(s, 6H), 3.4(d, 2H), 3.63(d, 2H), 4.55(t, 1H), 6.48(br, 2H), 8.33(s, 1H), 8.55 (t, 1H), 10.9(s, 1H) | 345 346 |
| 78 | Cl | —NH2 | 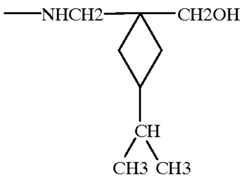 | —CH═NOH | 174–184 acetone | 0.78(d, 6H), 1.1–2.1(m, 6H), 3.2–3.8(m, 4H), 4.4(br, 1H), 6.51 (br, 2H), 8.39(s, 1H), 8.5(m, 1H), 10.85(s, 1H) | 327 328 |

TABLE 16-continued

| compound No. | R1 | R2 | R3 | R4 | m.p. (° C.) recrystallization solvent | $^1$H-NMR (60 MHz) | mass spectrum EIm/z CIm/z |
|---|---|---|---|---|---|---|---|
| 79 | Cl | —NH2 | 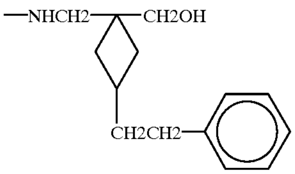 | —CH═NOH | 154–156 Et20 | 1.1–2.2(m, 7H), 2.5(t, 2H), 3.2–3.7(m, 4H), 4.4(br, 1H), 5.7(s, 2H), 7.15(s, 5H), 8.4(s, 1H), 8.5(t, 1H), 10.45(s, 1H) | 389 390 |
| 80 | Cl | —NH COCH3 | 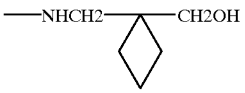 | H | 115–118 acetone | 1.75(s, 6H), 2.18(s, 3H), 3.2–3.6 (m, 4H), 4.52(t, 1H), 6.27(s, 1H), 7.62(t, 1H), 10.22(s, 1H) | 284 285 |

TABLE 17

| compound No. | R1 | R2 | R3 | R4 | m.p. (° C.) recrystallization solvent | $^1$H-NMR (60 MHz) | mass spectrum EIm/z CIm/z |
|---|---|---|---|---|---|---|---|
| 81 | —OH | —NH2 | 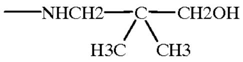 | H | 244–246 iso-PrOH | 0.82(s, 6H), 3.0(d, 2H), 3.1(d, 2H), 4.55(s, 1H), 6.15(s, 3H), 9.7(br, 1H) | 212 213 |
| 82 | —OH | —NH2 | 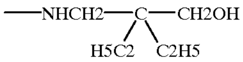 | H | 268–270 iso-PrOH | 0.78(t, 6H), 1.13(q, 4H), 2.97 (d, 2H), 3.15(br, 2H), 4.55(s, 1H), 4.68(br, 1H), 6.2(br, 3H), 9.8(br, 1H) | 240 241 |
| 83 | —OH | —NH2 | 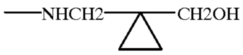 | H | 204–206 iso-PrOH | 0.4(s, 4H), 3.15(d, 2H), 3.35(s, 2H), 4.63(s, 1H), 6.23(br, 3H), 10.0(br, 1H) | 210 211 |
| 84 | —OH | —NH2 | 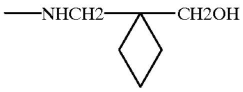 | H | 222–223 iso-PrOH | 2.0(s, 6H), 3.42(d, 2H), 3.6(br, 2H), 4.78(s, 1H), 4.8(br, 1H), 6.4(br, 2H), 6.5(t, 1H), 9.9(br, 1H) | 224 225 |
| 85 | —OH | —NH2 | 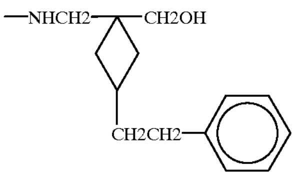 | H | 189–192 acetone —MeOH | 1.1–2.1(m, 7H), 2.5(t, 2H), 3.0–3.6(m, 4H), 4.6(s, 1H), 6.2(br, 3H), 7.18(s, 5H), 9.8(br, 1H) | 328 329 |

TABLE 18

| compound No. | R1 | R2 | R3 | R4 | m.p. (° C.) recrystallization solvent | $^1$H-NMR (60 MHz) | mass spectrum EIm/z CIm/z |
|---|---|---|---|---|---|---|---|
| 86 | —OCH3 | —NH2 | 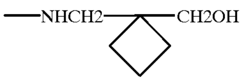 | H | 148–150 acetone | 1.78(br, 6H), 3.3(d, 2H), 3.38 (br, 2H), 3.73(s, 3H), 4.9(br, 1H), 5.13(s, 1H), 5.57(br, 2H), 6.35(t, 1H) | 238 239 |

TABLE 18-continued

| compound No. | R1 | R2 | R3 | R4 | m.p. (° C.) recrystallization solvent | $^1$H-NMR (60 MHz) | mass spectrum EIm/z CIm/z |
|---|---|---|---|---|---|---|---|
| 87 | 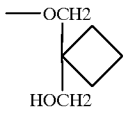 | —NH2 | 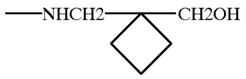 | H | 240–242 acetone | 1.8(br, 12H), 3.35(br, 6H), 4.1 (s, 2H), 4.55(t, 1H), 4.82(br, 1H), 5.13(s, 1H), 5.8(br, 2H), 6.45(t, 1H) | 322<br>323 |
| 88 | —CH3 | —NH2 | 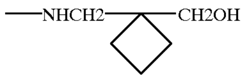 | H | 176–177 acetone | 1.70(s, 6H), 1.95(s, 3H), 3.20–3.40(m, 4H), 4.70(br, 1H), 5.59 (s, 1H), 5.70(s, 2H), 6.45–6.70 (t, 1H) | 222<br>223 |
| 89 | Cl | —NH2 | 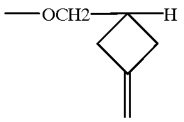 | H | 84–86 ligroin | 2.5–2.9(br, 4H), 4.25(d, 2H), 4.75(br, 2H), 5.4(br, 2H), 6.02 (s, 1H) (CDCl3) | 226<br>226 |
| 90 | Cl | —NH2 | 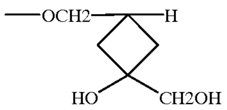 | H | 124–126 acetone | 1.9–2.2(m, 5H), 3.45(d, 2H), 4.25(d, 2H), 4.0–4.5(br, 2H), 6.0(s, 1H), 6.15(br, 2H) | 260<br>260 |

TABLE 19

| compound No. | R1 | R2 | R3 | R4 | m.p. (° C.) recrystallization solvent | $^1$H-NMR (60 MHz) | mass spectrum EIm/z CIm/z |
|---|---|---|---|---|---|---|---|
| 91 | Cl | —NH2 | 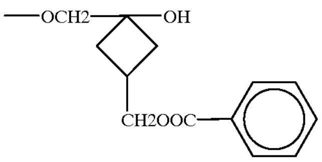 | H | — | 1.9–2.6(m, 5H), 3.4, 3.75(each s, 1H), 4.3(br, 4H), 6.0, 6.04 (each s, 1H), 7.2–8.1(m, 5H) (CDCl3) | 363<br>364 |
| 92 | Cl | —NH2 | 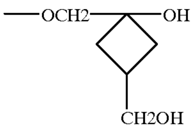 | H | 128–130 acetone | 1.7–2.4(m, 5H), 3.43(t, 2H), 4.14, 4.23(each s, 2H), 4.32(t, 1H), 4.98, 5.04(each s, 1H), 6.02(s, 1H), 6.67(br, 2H) | 260<br>261 |
| 93 | Cl | —NH2 | 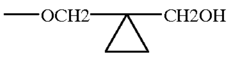 | H | 121–123 benzene | 0.60(s, 4H), 3.54(s, 2H), 4.30 (s, 2H), 4.70(s, 3H), 6.17(s, 1H) (CD3OD) | 229<br>230 |
| 94 | Cl | —NH2 | 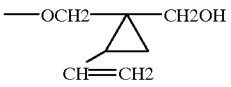 | H | 122–124 CH3CN | 0.6–1.1(m, 2H), 1.4–1.9(m, 1H), 3.45(d, 2H), 4.32(d, 2H), 4.54(t, 1H), 4.9–5.3(m, 2H), 5.35–6.0(m, 1H), 6.01(s, 1H), 6.65(br, 2H) | 255<br>256 |
| 95 | Cl | —NH2 | 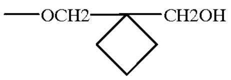 | H | 125–127 acetone | 1.85(br, 6H), 3.57(br, 3H), 4.25 (s, 2H), 5.75(br, 2H), 6.0(s, 1H) (CDCl3) | 243<br>244 |

TABLE 20

| compound No. | R1 | R2 | R3 | R4 | m.p. (° C.) recrystallization solvent | $^1$H-NMR (60 MHz) | mass spectrum EIm/z CIm/z |
|---|---|---|---|---|---|---|---|
| 96 | Cl | —NH2 | 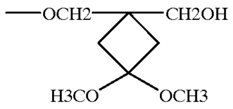 | H | 196–198 acetone | 1.95(s, 4H), 3.05(s, 6H), 3.45 (br, 2H), 4.2(s, 2H), 6.0(s, 1H), 6.85(br, 2H) | 304 304 |
| 97 | Cl | —NH2 | 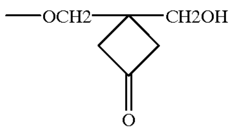 | H | 173–175 acetone | 2.97(s, 4H), 3.79(s, 2H), 4.52 (s, 2H), 4.73(s, 3H), 6.12(s, 1H) | 258 258 |
| 98 | Cl | —NH2 | 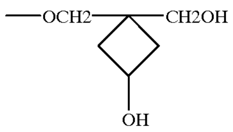 | H | 145–147 AcOEt | 1.6–2.4(m, 4H), 3.47(d, 2H), 4.25(s, 2H), 4.0–4.6(m, 2H), 4.82(d, 1H), 6.05(s, 1H), 6.45 (br, 2H) | 260 260 |
| 99 | Cl | —NH2 | 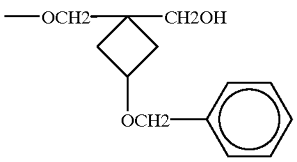 | H | 151–153 acetone | 1.7–2.4(m, 4H), 3.48(d, 2H), 4.22(s, 2H), 4.35(s, 2H), 3.95–4.6(m, 2H), 5.95(s, 1H), 6.37 (br, 2H), 7.28(s, 5H) | 349 350 |
| 100 | Cl | —NH2 | 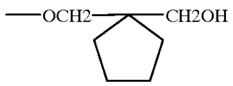 | H | 132–133 benzene | 1.6(br, 8H), 2.8(t, 1H), 3.4(d, 2H), 4.2(s, 2H), 5.2(br, 2H), 6.10(s, 1H) (CDCl3) | 257 258 |

TABLE 21

| compound No. | R1 | R2 | R3 | R4 | m.p. (° C.) recrystallization solvent | $^1$H-NMR (60 MHz) | mass spectrum EIm/z CIm/z |
|---|---|---|---|---|---|---|---|
| 101 | Cl | —NH2 | 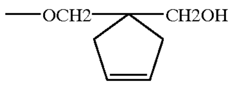 | H | 127–133 benzene | 2.25(s, 4H), 3.45(d, 2H), 4.27 (s, 2H), 5.1(br, 2H), 5.6(s, 2H), 6.1(s, 1H) | 255 256 |
| 102 | Cl | —NH2 | 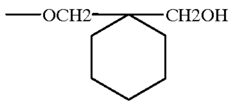 | H | 136–138 benzene | 1.47(s, 10H), 2.82(t, 1H), 3.45 (d, 2H), 4.20(s, 2H), 5.30(br, 2H), 6.10(s, 1H) (CDCl3) | 271 272 |
| 103 | —NH2 | —NH2 | 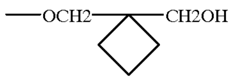 | H | 173–174 acetone | 1.84(br, 6H), 3.47(br, 2H), 4.1 (s, 2H), 4.55(br, 1H), 5.15(s, 1H), 5.8(br, 2H), 5.93(br, 2H) | 224 225 |
| 104 | —OH | —NH2 | 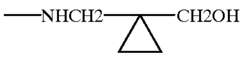 | —NH2 | 215–216 iso-PrOH | 0.4(s, 4H), 3.15(d, 2H), 3.35(s, 2H), 6.23(br, 5H), 10.0(br, 1H) | 225 226 |

TABLE 22

| compound No. | R1 | R2 | R3 | R4 | m.p. (° C.) recrystallization solvent | $^1$H-NMR (60 MHz) | mass spectrum EIm/z CIm/z |
|---|---|---|---|---|---|---|---|
| 105 | Cl | —NH2 | —NHCH2CH2OH | H | 143–146 CHCl3 | 3.43(br m, 2H), 3.66(t, 2H), 4.88(s, 4H), 5.86(s, 1H), (CD30D) | 188 190 |
| 106 | Cl | —NH2 | —NHCH2CH2OH.HCl | H | 173–176 Et20 | 3.58(t, 2H), 3.71(t, 2H), 4.94(s, 6H), 6.24(s, 1H), (CD30D) | 188 190 FAB 189 |
| 107 | Cl | —NH2 | —NHCH2CH2CH2OH | H | 160–163 EtOH | 1.55–2.1(m, 2H), 3.6(t, 4H), 6.33(s, 1H), 7.8(br, 3H), 9.3(br, 1H) | 202 203 |
| 108 | Cl | —NH2 | —NHCH2CH2CH2OH.HCl | H | 170–180 CHCl3—AcOEt | 1.50–2.1(m, 2H), 3.8(t, 4H), 6.33(s, 1H), 7.81(br, 3H), 9.0(br, 1H) | 202 203 |
| 109 | Cl | —NH2 | —NHCH2CH2CH2CH2OH | H | 139–141 MeOH | 1.52–1.69(m, 4H), 3.28–3.36 (m, 2H), 3.58(t, 2H), 4.89(br, 4H), 5.81(s, 1H) (CD30D) | 216 218 |

TABLE 23

| compound No. | R1 | R2 | R3 | R4 | m.p. (° C.) recrystallization solvent | $^1$H-NMR (60 MHz) | mass spectrum EIm/z CIm/z |
|---|---|---|---|---|---|---|---|
| 110 | Cl | —NH2 | —NHCH2CH2CH2CH2OH.HCl | H | 143–146 Et20 | 1.41–1.63(m, 4H), 3.36(br, 1H), 3.41(t, 4H), 6.14(br, 1H), 7.84(br, 2H), 8.93(br, 1H) | FAB 217 |
| 111 | Cl | —NH2 | —NHCH2CH2OH | —NH2 | 164–167 | 3.54(t, 2H), 3.70(t, 2H), 4.89(br, 6H) (CD30D) | 203 205 |
| 112 | Cl | —NH2 | —NHCH2CH2OH.2HCl | —NH2 | 158–161 Et20 | 3.50(br m, 2H), 3.60(t, 2H), 7.2(br m, 7H), 8.60(br m, 1H) | 203 205 FAB 204 |
| 113 | Cl | —NH2 | —NHCH2CH2CH2OH | —NH2 | 119–120 AcOEt | 1.6–2.1(m, 2H), 3.54(t, 2H), 3.67(t, 2H), 4.6(br, 6H) (CD30D) | 217 218 |
| 114 | Cl | —NH2 | —NHCH2CH2CH2OH.2HCl | —NH2 | 120–131 Et20 | 1.5–2.2(m, 2H), 3.5(t, 2H), 3.6(t, 2H), 4.6(br, 6H) | 217 218 |

TABLE 24

| compound No. | R1 | R2 | R3 | R4 | m.p. (° C.) recrystallization solvent | $^1$H-NMR (60 MHz) | mass spectrum EIm/z CIm/z |
|---|---|---|---|---|---|---|---|
| 115 | Cl | —NH2 | —NHCH2CH2CH2CH2OH | —NH2 | 58–62 MeOH | 1.54–1.74(m, 4H), 3.43(t, 2H), 3.59(t, 2H), 4.89(br, 6H) (CD30D) | FAB 232 |
| 116 | Cl | —NH2 | —NHCH2CH2CH2CH2OH.2HCl | —NH2 | 159–161 Et20 | 1.41–1.53(m, 2H), 1.56–1.67 (m, 2H), 3.39–3.47(m, 5H), 5.60(br, 2H), 7.27(br, 2H), 8.52(br, 1H) | FAB 232 |

TABLE 24-continued

| compound No. | R1 | R2 | R3 | R4 | m.p. (° C.) recrystallization solvent | $^1$H-NMR (60 MHz) | mass spectrum EIm/z CIm/z |
|---|---|---|---|---|---|---|---|
| 136 | Cl | —NH2 | 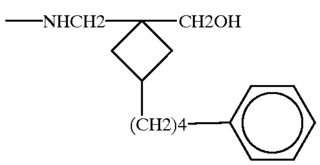 | H | 149–152 | 1.18–1.20(m, 2H), 1.36–1.38(m, 4H), 1.51–1.55(m, 2H), 1.78(m, 2H), 2.02–2.13(m, 1H),2.50–2.57(m, 2H), 3.22–3.37(m, 4H), 4.60(br, 1H), 5.81(s, 1H), 6.36 (s, 2H), 6.98(br, 1H), 7.15–7.26 (m, 5H) (300 MHz) | 374 375 |
| 137 | Cl | —NH2 | 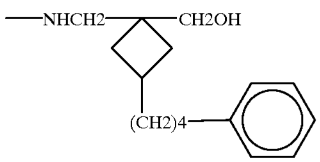 | —NH2 | 125–128 | 1.19(br, 2H), 1.38(br, 4H), 1.53 (br, 2H), 1.80(br, 2H), 2.08(br, 1H), 2.50(s, 2H), 3.21–3.47(m, 4H), 3.85(br, 2H), 4.60–4.67(m, 1H), 5.63(br, 2H), 6.37(br, 1H), 7.16–7.23(m, 5H) (300 MHz) | 389 390 |

PRODUCTION EXAMPLES OF INTERMEDIATES

METHOD K

PRODUCTION EXAMPLE 21, METHOD K-1

3-Phenylmethyloxy-1-hydroxymethyl-1-cyclobutylmethylamine (compound No. 123)

Step 1; Diethyl 3-phenylmethyloxy-1,1-cyclobutyldicarboxylate

Sodium (10.1 g, 0.44 mol) was dissolved in ethanol (220 ml) and 90 ml thereof was transferred to a dropping funnel. Diethyl malonate (42.3 g, 0.26 mol) was dropwise added to the remaining sodium ethylate solution. Then, sodium ethylate (90 ml) and 2-phenylmethyloxy-1,3-dibromopropane (67.39 g, 0.22 mol) were dropwise added simultaneously under refluxing, and the mixture was refluxed for 2 hours. The reaction mixture was filtered and the solvent in the filtrate was distilled away under reduced pressure. The residue was distilled under reduced pressure to give a colorless oil (32.16 g, 47.7%), b.p. 175–182° C./3 mmHg.

Step 2; 3-Phenylmethyloxy-1-ethoxycarbonyl-1-cyclobutylcarboxylic acid

Potassium hydroxide (6.5 g, 0.099 mol) was dissolved in 90% ethanol (500 ml) and diethyl 3-phenylmethyloxy-1,1-cyclobutyldicarboxylate (30.3 g, 0.099 mol) was added. The mixture was allowed to stand at room temperature for 3 days and the solvent was distilled away under reduced pressure. Water (100 ml) was added to the residue and the mixture was washed with ether. The aqueous layer was acidified with 10% hydrochloric acid, extracted with ether and dried over anhydrous magnesium sulfate. The solvent was distilled away under reduced pressure to give a colorless oil (24.47 g, 88.8%).

Step 3; Ethyl 3-phenylmethyloxy-1-carbamoyl-1-cyclobutylcarboxylate

3-Phenylmethyloxy-1-ethoxycarbonyl-1-cyclobutylcarboxylic acid (24.2 g, 0.087 mol) was dissolved in chloroform (400 ml). Triethylamine (8.8 g, 0.087 mol) was added under ice-cooling and ethyl chlorocarbonate (9.4 g, 0.087 mol) was added at 0° C. The mixture was stirred for 15 minutes and ammonia gas was introduced for 10 minutes. The mixture was stirred for 1 hour at room temperature and allowed to stand for one day. The reaction mixture was filtered and the filtrate was concentrated to give a colorless oil (25.0 g, 90.1%).

Step 4; 3-Phenylmethyloxy-1-hydroxymethyl-1-cyclobutylmethylamine $LiAlH_4$ (6.57 g, 0.173 mol) was suspended in dry tetrahydrofuran (200 ml) and ethyl 3-phenylmethyloxy-1-carbamoyl-1-cyclobutylcarboxylate (16.0 g, 0.0577 mol) dissolved in dry tetrahydrofuran (200 ml) was dropwise added thereto under ice-cooling. The mixture was refluxed for 5 hours. Water (17 ml), 10% potassium hydroxide (30 ml) and water (17 ml) were successively added dropwise under ice-cooling and the reaction mixture was filtered. Chloroform was added to the filtrate, and the mixture was washed with saturated brine and dried over anhydrous magnesium sulfate. The solvent was distilled away under reduced pressure to give a pale-yellow oil (10.5 g, 82.2%).

PRODUCTION EXAMPLE 22, METHOD K-2

3-Isopropyl-1-hydroxymethyl-1-cyclobutylmethylamine (compound No. 121)

Step 1; Diethyl 3-isopropyl-1,1-cyclobutyldicarboxylate

2-Isopropyl-1,3-propanediol di-p-toluenesulfonate (17.1 g, 0.04 mol) and diethyl malonate (7.05 g, 0.044 mol) were dissolved in dry dioxane (100 ml) and sodium hydride (1.6 g, 0.04 mol) suspended in dry dioxane (10 ml) was dropwise added thereto at 95–100° C. The mixture was stirred for 1 hour at the same temperature. Then, sodium hydride (1.6 g, 0.04 mol) suspended in dry dioxane (10 ml) was dropwise added thereto and the mixture was stirred at the same temperature for 20 hours. After cooling, the reaction mixture was filtered and the solvent in the filtrate was distilled away under reduced pressure. Ether was added to the residue, and the mixture was washed with water and dried over anhydrous magnesium sulfate. The solvent was distilled away under reduced pressure and the residue was purified by silica gel column chromatography (hexane:ethyl acetate=20:1) to give a colorless oil (6.14 g, 63.3%).

Step 2; 1-Ethoxycarbonyl-3-isopropyl-1-cyclobutylcarboxylic acid

To diethyl 3-isopropyl-1,1-cyclobutyldicarboxylate (6.06 g, 0.025 mol) was added sodium hydroxide (1.65 g, 0.025 mol) dissolved in 90% ethanol (125 ml), and the mixture was allowed to stand at room temperature for 3 days. The solvent was distilled away under reduced pressure and water was added to the residue. The mixture was washed with ether, neutralized with 10% hydrochloric acid under ice-cooling, extracted with ether and dried over anhydrous magnesium sulfate. The solvent was distilled away under reduced pressure to give a colorless oil (4.72 g, 88.1%).

Step 3; 1-Ethoxycarbonyl-3-isopropyl-1-cyclobutylcarboxamide

1-Ethoxycarbonyl-3-isopropyl-1-cyclobutylcarboxylic acid (4.5 g, 0.021 mol) was dissolved in chloroform (100 ml). Triethylamine (2.12 g, 0.021 mol) and ethyl chlorocarbonate (2.27 g, 0.021 mol) were added under ice-cooling and the mixture was stirred for 10 minutes. Ammonia gas was introduced for 5 minutes, and the mixture was stirred for one day at room temperature. The reaction mixture was filtered and the solvent in the filtrate was distilled away under reduced pressure. The residue was recrystallized from hexane to give colorless crystals (3.83 g, 85.5%).

Step 4; 3-Isopropyl-1-hydroxymethyl-1-cyclobutylmethylamine $LiAlH_4$ (1.94 g, 0.051 mol) was suspended in dry tetrahydrofuran (600 ml) and 1-ethoxycarbonyl-3-isopropyl-1-cyclobutylcarboxamide (3.63 g, 0.017 mol) dissolved in dry tetrahydrofuran (60 ml) was dropwise added thereto. The mixture was refluxed for 4 hours. Water (5 ml) and 10% potassium hydroxide (9 ml) were successively added dropwise under ice-cooling and the reaction mixture was filtered. The residue was washed with chloroform. The filtrate and the washing were combined and the mixture was dried over anhydrous magnesium sulfate. The solvent was distilled away under reduced pressure to give a colorless oil (2.67 g, quantitative).

METHOD L

PRODUCTION EXAMPLE 23

3-Phenylmethyloxy-1-hydroxymethyl-1-cyclobutylmethylamine (compound No. 123)

Step 1; Ethyl 3-phenylmethyloxy-1-carbamoyl-1-cyclobutylcarboxylate

3-Phenylmethyloxy-1-ethoxycarbonyl-1-cyclobutylcarboxylic acid (27.55 g, 0.1 mol) was dissolved in 100 ml of chloroform, and after cooling to not more than 0° C., thionyl chloride (15.5 g, 0.13 mol) was dropwise added, which was followed by reflux under heating for 1.5 hours. The reaction mixture was distilled under reduced pressure to give the objective slightly yellow oil (23.7 g, 0.079 mol). The obtained 3-phenylmethyloxy-1-ethoxycarbonyl-1-cyclobutylcarboxylic acid chloride was dissolved in 100 ml of chloroform, and after cooling to not more than −10° C., ammonia gas was introduced and the mixture was allowed to react at room temperature for 3 hours. The reaction mixture was washed with water and dried over anhydrous magnesium sulfate. The solvent was distilled away to give a colorless oil (21.6 g, 78%).

Step 2; 3-Phenylmethyloxy-1-hydroxymethyl-1-cyclobutylmethylamine $LiAlH_4$ (9.9 g, 0.26 mol) was suspended in dry tetrahydrofuran (250 ml) and ethyl 3-phenylmethyloxy-1-carbamoyl-1-cyclobutylcarboxylate (24.1 g, 0.087 mol) dissolved in dry tetrahydrofuran (200 ml) was dropwise added thereto under ice-cooling. The mixture was refluxed for 5 hours. Water (17 ml), 10% potassium hydroxide (45 ml) and water (26 ml) were successively added dropwise under ice-cooling and the reaction mixture was filtered. Chloroform was added to the filtrate, and the mixture was washed with saturated brine and dried over anhydrous magnesium sulfate. The solvent was distilled away under reduced pressure to give a pale-yellow oil (17.0 g, 88.3%).

METHOD M

PRODUCTION EXAMPLE 24

3-(2-Phenylethyl)-1-hydroxymethyl-1-cyclobutylmethylamine (compound No. 119)

Step 1; 1-Ethoxycarbonyl-3-(2-phenylethyl)-1-cyclobutylcarbonitrile

To a mixture of 2-(2-phenylethyl)-1,3-dibromopropane (21.4 g, 0.07 mol) and ethyl cyanoacetate (8.5 g, 0.07 mol) was added dropwise a solution of sodium (3.2 g, 0.14 mol) in ethanol (75 ml) at 70–75° C., and the mixture was refluxed for 3 hours and filtered. The solvent in the filtrate was distilled away under reduced pressure, and ether was added to the residue. The mixture was washed with water and dried over anhydrous magnesium sulfate. The solvent was distilled away under reduced pressure and the residue was purified by silica gel column chromatography (hexane:ethyl acetate=100:7) to give a colorless oil (9.3 g, 51.7%).

Step 2; 3-(2-Phenylethyl)-1-hydroxymethyl-1-cyclobutylmethylamine $LiAlH_4$ (3.98 g, 0.105 mol) was suspended in anhydrous ether (150 ml) and 1-ethoxycarbonyl-3-(2-phenylethyl)-1-cyclobutylcarbonitrile (9.0 g, 0.035 mol) dissolved in anhydrous ether (40 ml) was dropwise added thereto. The mixture was refluxed for 2 hours. Water (10 ml) and 10% potassium hydroxide (15 ml) were successively added dropwise under ice-cooling and the reaction mixture was filtered. The residue was washed with chloroform. The filtrate and the washing were combined and the mixture was dried over anhydrous magnesium sulfate. The solvent was distilled away under reduced pressure to give a colorless oil (7.1 g, 92.2%).

METHOD N

PRODUCTION EXAMPLE 25

3-(2-Phenylethyl)-1-(1-hydroxyethyl)-1-cyclobutylmethylamine (compound No. 127)

Step 1; 1-(Methylsulfinyl)methylcarbonyl-3-(2-phenylethyl)-1-cyclobutylcarbonitrile Dimethyl sulfoxide (8 ml) was added to 60% sodium hydride (0.72 g, 0.018 mol) and the mixture was stirred at 70° C. for 45 minutes. A solution of 1-ethoxycarbonyl-3-(2-phenylethyl)-1-cyclobutylcarbonitrile (3.86 g, 0.015 mol) in tetrahydrofuran (8 ml) was added under ice-cooling, and the mixture was stirred at room temperature for 30 minutes. The reaction mixture was poured into ice water (25 ml) and acidified with 10% hydrochloric acid. The mixture was extracted with chloroform, washed with water and dried over anhydrous magnesium sulfate. The solvent was distilled away under reduced pressure and the residue was purified by silica gel column chromatography (chloroform) to give white crystals (3.0 g, 69.1%), m.p. 77–83° C.

Step 2; 1-Acetyl-3-(2-phenylethyl)-1-cyclobutylcarbonitrile 1-(Methylsulfinyl)methylcarbonyl-3-(2-phenylethyl)-1-cyclobutylcarbonitrile (2.9 g, 0.01 mol) was dissolved in tetrahydrofuran (190 ml) and water (21 ml), and 2.7 g of aluminum amalgam (an aluminum sheet was dipped in 2% mercuric chloride for 15 seconds, washed with ethanol and ether and cut into 1 cm square for use) was added, which was followed by reflux for 1 hour and filtration through Celite. The solvent in the filtrate was distilled away under reduced pressure. The residue was extracted with ether, washed with water and dried over anhydrous magnesium sulfate. The solvent was distilled away under reduced pressure and the residue was purified by silica gel column chromatography (hexane:chloroform=2:1, later chloroform) to give a colorless oil (1.8 g, 79.3%).

Step 3; 3-(2-Phenylethyl)-1-(1-hydroxyethyl)-1-cyclobutylmethylamine $LiAlH_4$ (0.58 g, 15.2 mmol) was suspended in anhydrous ether (20 ml) and 1-acetyl-3-(2-phenylethyl)-1-cyclobutylcarbonitrile (1.73 g, 7.6 mmol) dissolved in anhydrous ether (10 ml) was dropwise added thereto. The mixture was refluxed for 2 hours. Water (15 ml) and 10% potassium hydroxide (20 ml) were successively added dropwise under ice-cooling and the reaction mixture was filtered. The residue was washed with chloroform. The filtrate and the washing were combined and the mixture was dried over anhydrous magnesium sulfate. The solvent was distilled away under reduced pressure to give white crystals (1.78 g, quantitative), m.p. 76–81° C.

METHOD P

PRODUCTION EXAMPLE 26

3-Hydroxymethyl-1-hydroxy-1-cyclobutylmethylamine (compound No. 130)

Step 1; 3-Benzoyloxymethyl-1-cyclobutylmethylene oxide

To a solution of 3-benzoyloxymethyl-1-methylenecyclobutane (10.1 g, 0.05 mol) in dry methylene chloride (40 ml) was added dropwise a solution of m-chloroperbenzoic acid in dry methylene chloride (100 ml), and the mixture was reacted with stirring at room temperature for one day. The reaction mixture was washed successively with 10% sodium bisulfite, saturated aqueous sodium hydrogencarbonate and saturated brine. The organic layer was dried over anhydrous magnesium sulfate. The solvent was distilled away and the residue was purified by silica gel column chromatography (hexane:ethyl acetate=20:1) to give a colorless oil (3.85 g, 35.3%).

Step 2; 3-Hydroxymethyl-1-hydroxy-1-cyclobutylmethylamine

3-Benzoyloxymethyl-1-cyclobutylmethylene oxide (1.83 g, 0.0084 mol) obtained in Step 1 was dissolved in a saturated ammonia-methanol solution (30 ml) and the mixture was allowed to react at room temperature for 4 days with stirring. The reaction mixture was concentrated under reduced pressure and the residue was purified by silica gel column chromatography (hexane:ethyl acetate=20:1) to give a colorless oil (0.93 g, 85%).

METHOD Q

PRODUCTION EXAMPLE 27

1-Hydroxymethyl-1-(N-methyl)cyclobutylmethylamine (compound No. 132)

1-Hydroxymethyl-1-cyclobutylmethylamine (1.15 g, 0.01 mol) was dissolved in 1.9 ml of formic acid and 0.2 ml of water, and 37% formalin (0.89 g, 0.011 mol) was added thereto, which was allowed to react at room temperature for 2 hours. Then, the mixture was reacted under heating for 7 more hours and at room temperature for 8 hours. The reaction mixture was concentrated to dryness under reduced pressure, and the residue was purified by silica gel column chromatography (chloroform:methanol=50:1) to give a colorless oil (1.0 g, 77.4%).

METHOD R

PRODUCTION EXAMPLE 28

1-Hydroxymethyl-1-(N-isobutyl)cyclobutylmethylamine (compound No. 133)

1-Hydroxymethyl-1-cyclobutylmethylamine (11.5 g, 0.1 mol) was dissolved in 50 ml of benzene, and 1-bromoisobutane and equimolar triethylamine were added thereto, which was followed by refluxing under heating for 5 hours. The reaction mixture was cooled, washed with water and dried over anhydrous magnesium sulfate, followed by concentration under reduced pressure. The residue was purified by silica gel column chromatography (chloroform:methanol=50:1) to give a colorless oil (14.3 g, 83.5%).

METHOD S

PRODUCTION EXAMPLE 29

1-Hydroxymethyl-1-cyclobutylamine (compound No. 135)

Step 1; 1-Ethoxycarbonyl-1-cyclobutylphenylmethyloxycarbonylamine

1-Ethoxycarbonyl-1-cyclobutylcarboxylic acid (3.44 g, 0.02 mol) was dissolved in dry benzene, and diphenylphosphoryl azide (5.5 g, 0.02 mol) and triethylamine (2.02 g, 0.02 mol) were added, which was followed by refluxing for 1 hour. Benzyl alcohol (2.45 g, 0.022 mol) was added and the mixture was refluxed for 13 hours. Thesolvent was distilled away under reduced pressure and the residue was dissolved in ethyl acetate. The mixture was washed successively with 5% hydrochloric acid, saturated aqueous sodium hydrogencarbonate and saturated brine, and dried over anhydrous magnesium sulfate. The solvent was distilled away under reduced pressure and the residue was purified by silica gel column chromatography (chloroform:hexane=1:1) to give a colorless oil (4.67 g, 84.1%).

Step 2; 1-Hydroxymethyl-1-cyclobutylphenylmethyloxycarbonylamine

1-Ethoxycarbonyl-1-cyclobutylphenylmethyloxycarbonylamine (2.77 g, 0.01 mol) was dissolved in dry tetrahydrofuran (5 ml), and lithium borohydride (0.33 g, 0.015 mol) dissolved in dry tetrahydrofuran was dropwise added. The mixture was stirred at room temperature for 1 hour. Then, 50% acetic acid (1 ml) was added under ice-cooling, and water (15 ml) was added, which was followed by extraction with ether. The residue was washed with saturated aqueous sodium hydrogencarbonate and saturated brine, and dried over anhydrous magnesium sulfate. The solvent was distilled away under reduced pressure to give a colorless oil (2.33 g, 99.1%).

Step 3; 1-Hydroxymethyl-1-cyclobutylamine

1-Hydroxymethyl-1-cyclobutylphenylmethyloxycarbonylamine (2.35 g, 0.01 mol) was dissolved in ethanol (100 ml), and palladium hydroxide (0.5 g) and cyclohexene (20 ml) were added. The mixture was refluxed for 1 hour and filtered. The solvent of the filtrate was distilled away under reduced pressure to give a colorless oil (1.0 g, quantitative).

The intermediates described in the foregoing Production Examples and the intermediates produced in the same manner as in the above Production Examples are shown in the following Tables.

TABLE 25

| compound No. | structural formula | m.p. (° C.) | $^1$H-NMR (60 MHz) |
|---|---|---|---|
| 117 | 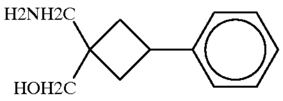 | 70–76 | 1.6–2.6(m, 4H), 2.7 (brs, 3H), 2.92, 3.1 (each s, 2H), 3.2–3.8 (m, 1H), 3.68, 3.88 (each s, 2H), 7.25(s, 5H) |
| 118 | 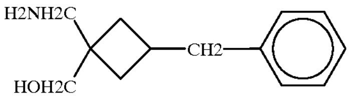 | oily substance | 1.2–2.3(m, 5H), 2.65 (brs, 2H), 2.9(brs, 3H), 2.8, 2.87(each s, 2H), 3.56, 3.65(each s, 2H), 7.14(s, 5H) |
| 119 | 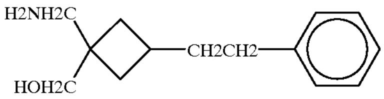 | oily substance | 1.1–2.3(m, 7H), 2.52(t, 2H), 2.65(brs, 3H), 2.83, 2.92(each s, 2H), 3.63, 3.73(each s, 2H), 7.25(s, 5H) |
| 120 | 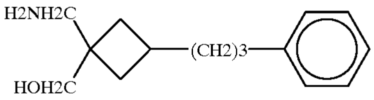 | oily substance | 1.0–2.3(m, 9H), 2.6 (brs, 2H), 3.0(brs, 3H), 2.88, 3.0(each s, 2H), 3.63, 3.76(each s, 2H), 7.27(s, 5H) |
| 121 | 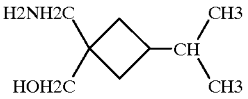 | oily substance | 0.8(d, 6H), 1.1–2.2(m, 6H), 2.8, 2.95(each s, 2H), 3.58, 3.73 (each s, 2H), 2.75(s, 3H) |

TABLE 26

| compound No. | structural formula | m.p. (° C.) | $^1$H-NMR (60 MHz) |
|---|---|---|---|
| 122 | 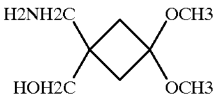 | oily substance | 1.95(s, 4H), 2.95(s, 2H), 3.17(s, 6H), 3.72(s, 2H), 2.7(s, 3H) |
| 123 | 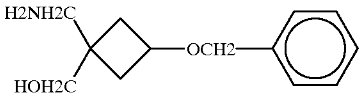 | oily substance | 1.5–2.5(m, 4H), 2.5(brs, 3H), 2.95(s, 2H), 3.67(s, 2H), 3.8–4.4(m, 1H), 4.4 (s, 2H), 7.35(s, 5H) |
| 124 | 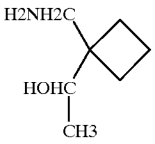 | oily substance | 1.2(d, 3H), 1.4–2.2(m, 6H), 2.85(brs, 3H), 3.01 (d, 1H), 3.17(d, 1H), 3.99 (q, 1H) |
| 125 | 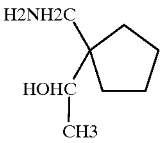 | 36–39 | 1.2(d, 3H), 1.6(brs, 8H), 2.9(brs, 3H), 2.75(d, 1H), 2.99(d, 1H), 3.82(q, 1H) |

TABLE 26-continued

| compound No. | structural formula | m.p. (° C.) | $^1$H-NMR (60 MHz) |
|---|---|---|---|
| 126 | 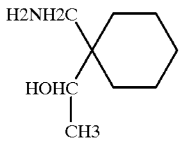 | 36–39 | 1.2(d, 3H), 1.55(brs, 10H), 3.0(brs, 3H), 2.81 (d, 1H), 3.07(d, 1H), 3.83 (q, 1H) |

TABLE 27

| compound No. | structural formula | m.p. (° C.) | $^1$H-NMR (60 MHz) |
|---|---|---|---|
| 127 | 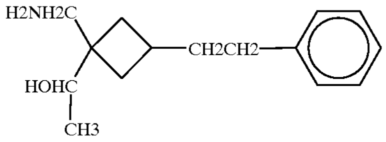 | 76–81 | 1.2(d, 3H), 1.5–2.3(m, 7H), 2.52(t, 2H), 2.85 (brs, 3H), 3.01(d, 1H), 3.16(d, 1H), 3.99(q, 1H), 7.25(s, 5H) |
| 128 | 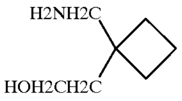 | oily substance | 1.5–2.0(m, 8H), 2.68(s, 2H), 3.22(brs, 3H), 3.47(t, 2H) |
| 129 | 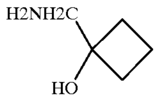 | oily substance | 1.6–2.5(m, 6H), 2.59, 2.65(each s, 2H), 4.65 (s, 3H) |
| 130 | 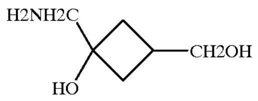 | oily substance | 1.6–2.4(m, 5H), 2.59, 2.65(each s, 2H), 3.5 (d, 2H), 4.65(s, 4H) |
| 131 | 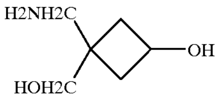 | oily substance | 1.4–2.5(m, 4H), 2.71(s, 2H), 3.51(s, 2H), 3.9–4.5(m, 1H), 4.7(s, 4H) (CD30D) |

TABLE 28

| compound No. | structural formula | m.p. (° C.) | $^1$H-NMR (60 MHz) |
|---|---|---|---|
| 132 | 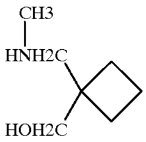 | oily substance | 1.82(s, 6H), 2.19(s, 3H), 2.45(s, 2H), 3.73(s, 2H), 4.38(brs, 2H) |

TABLE 28-continued

| compound No. | structural formula | m.p. (° C.) | $^1$H-NMR (60 MHz) |
|---|---|---|---|
| 133 | 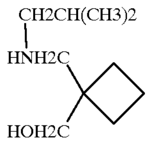 | oily substance | 0.9(d, 6H), 1.2–2.1(m, 7H), 2.38(d, 2H), 2.8(s, 2H), 3.7(s, 2H) |
| 134 | 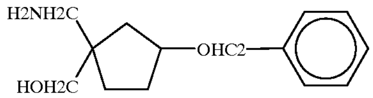 | oily substance | 1.3–2.5(m, 6H), 2.4(brs, 3H), 3.67(s, 2H), 3.8–4.4(m, 1H), 4.5(s, 2H), 7.35(s, 5H) |
| 135 | 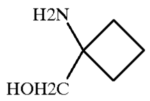 | oily substance | 1.6–2.3(m, 6H), 2.5(s, 3H), 3.5(s, 2H) |

EXPERIMENTAL EXAMPLES

Determination of anti-rotaviral activity

The method of determination of the anti-rotaviral activity and toxicity of the compound of the present invention, and the results obtained are shown in the following.

Experimental Example 1

Determination of activity of test compound against rotavirus and evaluation thereof The virus and cells used for the assay were prepared as in the following.

rotavirus: To a liquid containing preserved rotavirus SA-11 strain was added trypsin (Sigma, acetylated trypsin type V-S) to 10 μg/ml and incubated at 37° C. for 30 minutes to activate the cells, after which the culture was diluted to a concentration of 50 plaque forming units (PFU)/0.1 ml with Eagle's minimum essential medium (MEM) and used for the determination.

cultured cell: CV-1 cells which are green monkey kidney cell line were cultured in MEM supplemented with 10% calf serum. The culture cells were prepared to a concentration of $4\times10^5$ cells/ml, plated on a 24 well microplate and cultured for 2 days before use for the determination.

1. Determination of antiviral activity (50% plaque reduction method)

Activated rotavirus SA-11 cells were inoculated at 50 PFU/0.1 ml to CV-1 cells cultured in a monolayer on a 24 well microplate. The virus was allowed to adsorb to the cells in 1.5 hours at 37° C. and the surface layer of the cells was washed three times with MEM. Then, a multilayer agar medium (mixed medium of MEM, 3 μg/ml acetylated trypsin and agar at final concentration of 0.8%, all added at 45° C.) containing aliquot of test compounds was superposed on the cell layer. The cells were incubated at 37° C. for 4 days, immobilized with formalin, stained with a crystal violet solution and counted for plaque number.

The antiviral activity was expressed by the concentration of the test compound (50% plaque inhibition dose: $ID_{50}$= μg/ml), which decreased plaques formed in the control cell culture without the test compound, by 50%.

2. Determination of cytotoxicity (50% cell growth inhibition effect)

CV-1 cells were prepared to a concentration of $4\times10^4$ cells/ml with MEM containing 10% calf serum and plated on a 24 well microplate, which was followed by culture for 2 days. The culture solution thereof was changed to MEM containing 10% calf serum and serially diluted test compounds at various concentrations, and the cells were cultured for 2 days. The cells were prepared into a homogeneous single cell suspension using 0.1% crude trypsin, and counted with a Coulter counter Model D (Coulter Electronics Ltd., England).

The 50% cell growth inhibition effect dose ($ED_{50}$=μg/ml) was expressed by the concentration of the test compound, which decreased cell numbers in the control cell culture without the test compound, by 50%.

3. Antiviral index $ED_{50}$ value was divided by $ID_{50}$ value and the obtained value was used as an antiviral index for the determination of selective anti-rotaviral activity on infected cells in comparison to that on normal cells (host cells).

The results are shown in Table 29. As shown in Table 29, every test compound showed superior anti-rotaviral activity.

TABLE 29

| compound No. | rotavirus SA-11 cells $ID_{50}$ = μg/ml | CV-1 cells $ED_{50}$ = μg/ml | antiviral index ($ED_{50}/ID_{50}$) |
|---|---|---|---|
| 3 | 12.6 | | |
| 6 | 2.9 | | |
| 20 | 10.5 | >1.00 | >9.5 |
| 23 | 3.5 | 80 | 23 |
| 24 | 1.1 | 56.2 | 51.1 |
| 25 | 0.2 | 30.0 | 150.0 |
| 28 | 3.0 | >30 | >10 |
| 35 | 7.8 | | |
| 58 | 1.5 | >100 | >67 |
| 59 | 1.9 | 3.6 | 2 |
| 86 | 2.2 | | |
| 104 | 0.6 | | |
| 113 | 2.6 | >100 | >38 |

Experimental Example 2

Toxicity test

A test compound was orally administered to male ICR mice (weight 25–35 g) fasted overnight, and survival thereof was monitored for 14 days. The results are shown using minimum lethal dose in Table 30. As shown in Table 30, every compound showed a low toxicity value.

TABLE 30

| compound No. | mouse acute toxicity [lethal dose] (mg/kg-po) | compound No. | mouse acute toxicity [lethal dose] (mg/kg-po) |
|---|---|---|---|
| 5 | [>500] | 47 | [>500] |
| 6 | [>500] | 48 | [>500] |
| 7 | [>500] | 58 | [>1000] |
| 18 | [>500] | 59 | [>500] |
| 35 | [>500] | 104 | [>1000] |
| 39 | [>500] | 112 | [>1000] |
| 43 | [>500] | 113 | [>1000] |
| 44 | [>500] | | |

The formulation of preparation is as follows.

The compounds of the present invention can be administered in 0.1–1000 mg per body weight (kg). These compounds can be administered in the dosage form of tablet or capsule. As long as their solubility permits, they can be administered as a water soluble syrup, oily solution or when the compound is insoluble, as a suspension. Typical formulations of pharmaceuticals are shown in the following.

| | |
|---|---|
| Capsules | |
| Compound of invention | 0.1–500 mg |
| Abicel PH-101 (microcrystalline cellulose) | amount to make the total 800 mg |
| Tablets | |
| Compound of invention | 0.1–500 mg |
| Abicel PH-101 | 130 mg |
| Starch (modified) | 20 mg |
| Magnesium stearate | 5.5 mg |
| Polyvinylpyrrolidone | 22 mg |
| Stearic acid | 30 mg |

What is claimed is:

1. A pyrimidine compound of the formula (I)

(I)

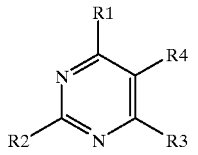

wherein

R1 is H, $C_1$–$C_4$ alkyl, halogen atom, —OH, $C_1$–$C_4$ alkoxy, $C_1$–$C_6$ hydroxyalkoxy or —$NH_2$;

R2 is —$NH_2$ or —$NHCOCH_3$;

R3 is —$NR5(CH_2)_i$—$CH_2OH$;

R4 is H, halogen atom, —$NH_2$, —CN, —CHO, —$CH_2OH$, —COOH, —$CH_2NH_2$, —$CONH_2$ or —CH═N—A, wherein A is —OH, $C_1$–$C_4$ alkyl or $C_1$–$C_4$ alkoxy;

R5 is H; and i is an integer of 1 to 4, or a pharmacologically acceptable salt thereof.

2. A pharmaceutical composition comprising a pyrimidine compound of claim 1 or a pharmacologically acceptable salt thereof and a pharmacologically acceptable carrier.

3. A method for the prophylaxis and treatment of diseases in a host caused by infection by rotaviruses, which comprises administering to a host an effective amount of a pyrimidine compound of claim 1 or a pharmacologically acceptable salt thereof.

4. A method for the prophylaxis and treatment of diseases in a host caused by infection by rotaviruses, which comprises administering to a host an effective amount of a pyrimidine compound of the formula (I)

(I)

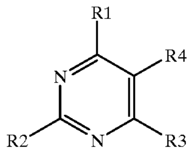

wherein

R1 is H, $C_1$–$C_4$ alkyl, halogen atom, —OH, $C_1$–$C_4$ alkoxy, $C_1$–$C_6$ hydroxyalkoxy or —$NH_2$;

R2 is H, —$NH_2$ or —$NHCOCH_3$;

R3 is —$NR5(CH_2)_i$—$CH_2OH$;

R4 is H, halogen atom, —$NH_2$, —CN, —CHO, —$CH_2OH$, —COOH, —$CH_2NH_2$, —$CONH_2$ or —CH═N—A wherein A is —OH, $C_1$–$C_4$ alkyl or $C_1$–$C_4$ alkoxy;

R5 is H or $C_1$–$C_4$ lower alkyl; and i is an integer of 1 to 4, or a pharmacologically acceptable salt thereof.

5. A method for the prophylaxis and treatment of diseases in a host caused by infection by rotaviruses, which comprises administering to a host an effective amount of pyrimidine compound of the formula (I')

[I']

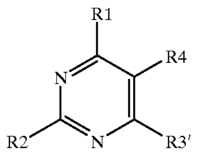

wherein

R1 is H, $C_1$–$C_4$ alkyl, halogen atom, —OH, $C_1$–$C_4$ alkoxy, $C_1$–$C_6$ hydroxyalkoxy or —$NH_2$;

R2 is H, —$NH_2$ or —$NHCOCH_3$;

R3' is a group selected from the group consisting of the following (a) to (e):

(a)

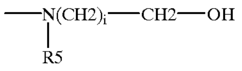

(b)

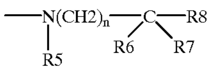

(c)

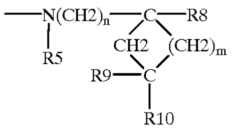

-continued (d)

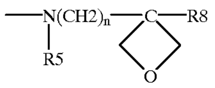

(e)

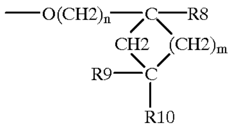

wherein

R5 is H or $C_1$–$C_4$ lower alkyl,

R6 and R7 are the same or different and each is $C_1$–$C_4$ lower alkyl,

R8 is H, —OH, $C_1$–$C_4$ hydroxyalkyl or —$CH_2OC(O)CH_3$,

R9 is H, —OH, $C_1$–$C_4$ alkyl, $C_1$–$C_4$ hydroxyalkyl, $C_1$–$C_4$ lower alkoxy, vinyl, —$O(CH_2)_k$—R where R is aromatic ring optionally having, on its ring, a substituent selected from the group consisting of $C_1$–$C_4$ alkyl, halogen atom and $C_1$–$C_4$ alkoxy, and k is an integer of 0 to 4, or —$(CH_2)_j$—R', where R' is benzoyloxy or aromatic ring optionally having, on its ring, a substituent selected from $C_1$–$C_4$ lower alkyl, halogen atom, and $C_1$–$C_4$ alkoxy, and j is an integer of 0 to 6, R10 is H, —OH or $C_1$–$C_4$ alkoxy, R9 and R10 may form a methylene group (=$CH_2$) or a carbonyl (C=O) together with the carbon atom to which they are bonded, in the formulas (c) and (e), cycloalkyl ring may have a double bond at an optional position in the ring, i is an integer of 1 to 4, n is an integer of 0 to 4, and m is an integer of 0 to 4; and R4 is H, halogen atom, —$NH_2$, —CN, —CHO, —$CH_2OH$, —COOH, —$CH_2NH_2$, —$CONH_2$ or —CH=N—A where A is —OH, $C_1$–$C_4$ alkyl or $C_1$–$C_4$ alkoxy, exclusive of when n is 0 and R8 is H;

or a pharmacologically acceptable salt thereof.

6. The method of claim 5, wherein j is an integer of 0 to 4.

* * * * *

UNITED STATES PATENT AND TRADEMARK OFFICE

CERTIFICATE OF CORRECTION

PATENT NO. : 6,080,750
DATED : June 27, 2000
INVENTOR(S) : Hisaki et al.

It is certified that error appears in the above-identified patent and that said Letters Patent is hereby corrected as shown below:

Column 12,
Line 16, "n=O" should read -- n=0 --.

Column 14,
Line 62, "from 10°C" should read -- from -10°C --.

Column 17,
Line 4, "R120H" should read -- R12OH --.

Column 68,
Table 29, in the row of Compound No. 20, and column of CV-1 cells $ED_{50}$=µg/ml: ">1.00" should read -- >100 --.

Claim 1, column 69,
Line 60, "i is an integer of 1 to 4," should read -- i is 1 or 2, --.

Signed and Sealed this

Thirtieth Day of October, 2001

*Attest:*

Nicholas P. Godici

NICHOLAS P. GODICI

*Attesting Officer* *Acting Director of the United States Patent and Trademark Office*